(12) United States Patent
Österlund et al.

(10) Patent No.: US 9,709,504 B2
(45) Date of Patent: Jul. 18, 2017

(54) OPTICAL SENSOR UNIT FOR EVANESCENCE WAVE SPECTROSCOPY

(75) Inventors: Lars Österlund, Umeå (SE); Per Ola Andersson, Umeå (SE); Mikael Karlsson, Uppsala (SE); Fredrik Nikolajeff, Stockholm (SE)

(73) Assignee: MOLECULAR FINGERPRINT SWEDEN AB, Uppsala (SE)

( * ) Notice: Subject to any disclaimer, the term of this patent is extended or adjusted under 35 U.S.C. 154(b) by 358 days.

(21) Appl. No.: 12/989,024

(22) PCT Filed: Apr. 22, 2009

(86) PCT No.: PCT/SE2009/050419
§ 371 (c)(1),
(2), (4) Date: Jan. 3, 2011

(87) PCT Pub. No.: WO2009/131535
PCT Pub. Date: Oct. 29, 2009

(65) Prior Publication Data
US 2011/0090484 A1    Apr. 21, 2011

Related U.S. Application Data

(60) Provisional application No. 61/047,191, filed on Apr. 23, 2008.

(51) Int. Cl.
*G01J 5/20*    (2006.01)
*G01N 21/77*    (2006.01)
(Continued)

(52) U.S. Cl.
CPC ..... *G01N 21/7703* (2013.01); *G01N 21/3577* (2013.01); *G01N 21/552* (2013.01); *G02B 6/102* (2013.01); *G02B 2006/12035* (2013.01)

(58) Field of Classification Search
CPC ... G01N 21/552; G01N 21/3577; G01N 21/35
(Continued)

(56) References Cited

U.S. PATENT DOCUMENTS 5,552,272 A    9/1996    Bogart
5,616,922 A    4/1997    Reffner et al.
(Continued)

FOREIGN PATENT DOCUMENTS

EP    0786665 A1    7/1997
JP    64-056401 A    3/1989
(Continued)

OTHER PUBLICATIONS

FT-IR Spectroscopy Attenuated Total Reflectance published by PerkinElmer (2005), p. 1-5 available at http://www.utsc.utoronto.ca/~traceslab/ATR_FTIR.pdf.*
(Continued)

*Primary Examiner* — David J Makiya
*Assistant Examiner* — Kenneth J Malkowski
(74) *Attorney, Agent, or Firm* — Porter Wright Morris & Arthur LLP

(57) ABSTRACT

Optical sensor unit for infra red evanescence wave spectroscopy (IR-EWS) analysis of chemical and biological substances in an analyte, comprising a waveguide with a sensor surface to be put into contact with the analyte, wherein the sensor surface is provided with an affinity enhancing layer. There is further provided a method of producing an optical sensor unit.

17 Claims, 19 Drawing Sheets

(51) Int. Cl.
  *G01N 21/552* (2014.01)
  *G01N 21/3577* (2014.01)
  *G02B 6/10* (2006.01)
  *G02B 6/12* (2006.01)

(58) Field of Classification Search
  USPC .................................................. 250/338.4
  See application file for complete search history.

(56) References Cited

U.S. PATENT DOCUMENTS

| 7,978,331 | B2 | 7/2011 | Higashi et al. | |
|---|---|---|---|---|
| 2002/0190213 | A1 | 12/2002 | Bynum et al. | |
| 2003/0176002 | A1* | 9/2003 | Zhang et al. | 438/22 |
| 2004/0121491 | A1 | 6/2004 | Marchand-Brynaert et al. | |
| 2007/0176093 | A1* | 8/2007 | Kukla et al. | 250/288 |

FOREIGN PATENT DOCUMENTS

| WO | 00/04364 A2 | 1/2000 |
|---|---|---|
| WO | 2007/108328 A1 | 9/2007 |

OTHER PUBLICATIONS

Nanocrystalline diamond films synthesized at low temperature and low pressure by hot filament chemical vapor deposition, Surface and Coatings Technology 201 (2006), 801-806, to Hao et al.*
Remes, The RF plasma surface chemical modification of nanodiamond films grown on glass and silicon at low temperature, Diamond and Related Materials (2007), 16:671-674.
Andersson, et al., "A Novel ATR-FTIR Approach for Characterisation and Identification of Ex Situ Immobilised Species", ChemPhysChem, 2007, vol. 8, 712-722.
Branan, et al., "Microorganism characterization using ATR-FTIR on an ultrathin polystyrene layer", Vibrational Spectroscopy, 2007, vol. 44, 192-196.
Buffeteau, et al., "Quantitative Orientation of α-Helical Polypeptides by Attenuated Total Reflection Infrared Spectroscopy", J. Phys. Chem B, 2001, vol. 105, 1464-1471.
Chang, et al., "Experimental Observation of 10.6-μm Guided Waves in Ge Thin Films", Applied Optics, 1971, vol. 10, 2361.
Chittur, "FTIR/ATR for protein adsorption to biomaterial surfaces", Biomaterials, 1998, vol. 19, 357-369.
Clarke, et al., "Conformational Changes of Fibrinogen after Adsorption", J. Phys. Chem B, 2005, vol. 109, 22027-22035.
Cottier, et al., "Thickness-modulated waveguides for integrated optical sensing", Optical Fibers and Sensors for Medical Applications II, 2002, vol. 4616, 53-63.
Hao, et al., "Nano-crystalline diamond films synthesized at low temperature and low pressure by hot filament chemical vapor deposition", Surface & Coatings Technology 2006, 201, 801-806.
Härtl, et al, "Protein-modified nanocrystalline diamond thin films for biosensor applications", Nature Materials, 2004, vol. 3, 736-742.
Herron, et al., "Planar Waveguide Biosensors for Nucleic Acid Hybridization Reactions", In-Vitro Diagnostic Instrumentation, Proceedings of SPIE, 2000, vol. 3913, 177-184.
Konov, et al., "Nanocrystalline diamond films—new material for IR optics", SPIE, 1995, vol. 2428, 612-620.
Karlsson, et al., "Transfer of continuous-relief diffractive structures into diamond by use of inductively coupled plasma dry etching", Optics Letters, 2001, vol. 26, 1752-1754.
Khabashesku, et al., "Functionalized carbon nanotubes and nanodiamonds for engineering and biomedical applications", Elsevier Science Sa, 2005, vol. 14, 859-866.
Kosower, et al., "Surface-Enhanced Infrared Absorption and Amplified Spectra on Planar Silver Halide Fiber", Journal of Physical Chem B, 2004, vol. 108, 12633-12636.
Liao, et al., "FTIR-ATR detection of proteins and small molecules through DNA conjugation", Sensors and Actuators B Chemical, 2006, vol. 114, 445-450.
Nabok, et al., "Registration of heavy metal ions and pesticides with ATR planar waveguide enzyme sensors", Elsevier Science Bv, 2004, 423-428.
Nebel, et al., "Diamond for bio-sensor applications", Journal of Physics D: Applied Physics, 2007, vol. 40, 6443-6466.
Plunkett, et al., Supported planar germanium waveguides for infrared evanescent-wave sensing, Applied Optics, 1997, vol. 36, 4055-4061.
Reiter, et al., "In Situ FTIR ATR spectroscopic study of the interaction of immobilized human tumor necrosis factor -α with a monoclonal antibody in aqueous environment", Biochimica et Biophysica Acta-Proteins and Proteomics, 2004, vol. 1699, 253-261.
Remes, et al., "Nanocrystalline diamond surface functionalization in radio frequency plasma", Diamonds & Related Materials, 2006, vol. 15, 745-748.
Rigler, et al., "Reversible Immobilization of Peptides: Surface Modification and In Situ Detection by Attenuated Total Reflection FTIR Spectroscopy", Chemphyschem, 2003, vol. 4, 268-275.
Vigano et al, "Detection of structural and functional asymmetries in P-glycoprotein by combining mutagenesis and H/D exchange measurements", Elsevier Sci Ireland Ltd., 2003, 121-135.
Rigler, et al., "Downscaling Fourier Transform Infrared Spectroscopy to the Micrometer and Nanogram Scale: Secondary Structure of Serotonin and Acetylcholine Receptors", Biochemistry, 2003, vol. 42, 14017-14022.
Schneider, et al., "High pressure view-cell for simultaneous in situ infrared spectroscopy and phase behavior monitoring of multiphase chemical reactions", Review of Scientific Instruments, 2003, vol. 74, 4121-4128.
Siebert, et al., "Infrared integrated optical evanescent field sensor for gas analysis Part I; System design", Sensors and Actuators A: Physical, 2005, vol. 119, 138-149.
Siebert, et al., "Infrared integrated optical evanescent field sensor for gas analysis Part II. Fabrication", Sensors and Actuators A: Physical, 2005, vol. 119, 584-592.
Smith, et al., "Covalent Attachment of a Nickel Nitrilotriacetic Acid Group to a Germanium Attenuated Total Reflectance Element", Langmuir, 2004, vol. 20, 1184-1188.
Wenzl, et al., "Supported Phospholipid Bilayers Prepared by the "LB/ Vesicle Method": A Fourier Transform Infrared Attenuated Total Reflection Spectroscopic Study on Structure and Stability", Langmuir, 1994, vol. 10, 4253-4264.
Vongsvivut, et al., "Symmetrically Tapered <30-μm-thickQuasi-Planar Germanium Waveguides as Chemical Sensors for Microanalysis", Applied Spectroscopy, 2002, vol. 56, 1552-1561.
Williams, et al., "Comparison of the growth and properties of ultrananocrystalline diamond and nanocrystalline diamond", Diamond and Related Materials, 2006, vol. 15, 654-658.
Yang, et al., "DNA-modified nanocrystalline diamond thin-films as stable, biologically active substrates", Nature Materials, 2002, vol. 1, 253-257, 1.
Yokoyama, et al., "Quantitive analysis of protein adsorption on a planar surface by Fourier transform infrared spectroscopy: lysozyme adsorbed hydrophobic silicon-containing polymer", Journal of Colloidal Science, 2003, vol. 268, 23-32.

* cited by examiner

OPTICAL SENSOR UNIT FOR EVANESCENCE WAVE SPECTROSCOPY

The present application is a 371 of PCT/SE2009/050419 filed Apr. 22, 2009 and claims priority under 35 U.S.C. 119 of U.S. Application No. 61/047,191 filed Apr. 23, 2008.

The present invention relates to the art of evanescence wave spectroscopy analysis of chemical and biological substances in an analyte, and in particular to an optical sensor unit for evanescence wave spectroscopy.

BACKGROUND TO THE INVENTION

There is a huge demand of new types of sensor surfaces and devices that can readily be functionalized for sensitive, selective and quantitative analysis of broad spectrum chemical and biological substances. It is desirable to study real-time molecular interactions, preferable in situ or even in vivo. This is important not only since this opens up the possibility for immediate signal read-out (high throughput), but also because it gives additional information of the kinetics and discrimination of multiple molecular binding. At the same time these sensor surfaces and devices should be suitable for repeated usage (mechanical and chemical stable), function in a wide range of environmental conditions (pH, temperature, pressure, and chemical environment), and yield reproducible results with minimum of recondition or sample preparation. Preferably, they should be made of materials that are amenable for easy and reproducible production, miniaturization, safe operation, high throughput, and ultimately biocompatible. For example, in disease diagnosis detection of multiple biomarkers is important in the diagnosis of complex diseases like cancer and neurological disorder. The use of devices capable of multiple markers detection in healthcare applications requires detection techniques with transducer materials that are selective, sensitive and biocompatible. Current transducer materials like polystyrene beads, carbon electrodes, gold, silicon, oxidized silicon and glass do not meet the requirements of smoothness, homogeneity, chemical and electrical stability, reproducibility, and biochemical surface modifications, and are not amenable for bio-integration [1].

There are a number of sensor devices and surface sensitive techniques available today which are capable of specific bio- and chemical sensing. The most common are sensitive to changes of mass (quartz crystal microbalance, QCM), refractive index (surface plasmon resonance, SPR), or fluorescent properties. [2-4] In general, all these techniques are based on the same detection principle, namely bonding of the analyte to specific (receptor) sites at the sensor surface. These methods can yield molecular information such as chemical identity, concentration, binding affinity, conformational properties, visco-elastic properties and thermodynamic parameters. Drawbacks with current commercial techniques include poor sensitivity toward small molecules (SPR and QCM), and unspecific analyte binding. Fluorescent techniques rely on changes of fluorescent properties, which work well for some molecules but not for others; otherwise tedious additions of fluorescent labels are required, which can interfere with molecular binding or make interpretation ambiguous.

A useful and surface sensitive optical technique is attenuated total reflection (ATR) spectroscopy. This is based on internal reflection in a material, or internal reflection element (IRE), with high refractive index, $n_{IRE}$, which is much higher than the surrounding medium, typically $n_{IRE} > 2$ [5]. The electromagnetic waves that propagate inside the IRE produce an evanescent field across the interfaces to the surrounding media (with $n \ll n_{IRE}$) and may loose or gain energy by resonant excitation in the evanescent field region that penetrates into the adjacent low refractive index medium surrounding the IRE. The penetration length of the evanescent field, $d_p$, depends on the angle of incidence ($\theta_1$) and the ratio of the refractive index of the waveguide and the surrounding medium. The ability of molecules in the immediate vicinity outside the IRE to absorb energy from the light propagating within the IRE by the evanescent field is the basis for all evanescence-wave spectroscopy (EWS) methods, which includes ATR spectroscopy. Fluorescent (TIRF), microwave, UV-vis, near-infrared, or mid-infrared (ATR-IR) spectroscopy may be performed in this way. A great advantage with EWS is that it can be used to study any molecule, independent of state of aggregation, size, charge, or fluorescent properties. In addition, it can give specific chemical interactions that unravel chemical interactions. The ATR-IR spectroscopy has been revolutionized by single or multiple reflection elements (MREs) combined with anvil-type pressing devices that allow virtually any type of samples to be analyzed with minimum sample preparation. In particular diamond is attractive. Apart from having the desired optical properties (broad band optical transmittivity and high refractive index; n=2.4), it has superior mechanical (large Young's modulus), thermal (high thermal conductivity) and chemical properties (it is chemical inert; it can operate in at all pH and temperature intervals of interest) that makes it the standard IRE material in most laboratories. ATR-IR has proved to be useful in a wide variety of applications, including chemical [6-8] and biological (protein, bacterial) identification [6; 9; 10], biosensors [2; 11; 12], catalysis [13], etc.

Diamond is also an attractive optical material for photonic and optoelectronic applications with advantageous broad band transmitting and intrinsic narrow band emission (e.g. due to N-V centers) properties. Developments in fabrication methods show that high-quality diamond can be produced and manipulated with great precision. The additional beneficial abovementioned physic-chemical properties thus make diamond a very promising material in future microelectronic and photonic application. Nanocrystalline diamond (NCD) or ultra-nanocrystalline diamond (UNCD) is a form of diamond where the grain size of crystallites is in the order of nanometer. Thin NCD films grown on Si substrates from methane-hydrogen gas mixture in a DC arc plasma CVD reactor yield optical transparency greater than 84% at $\lambda > 700$ nm [14]. Surface roughness in the order of 5-50 nm for 1 μm thick films, significantly decrease the transmission in the visible because of light scattering, but has negligible effect in the IR range. NCD films are transparent in the IR and have optical constants n=2.34-2.36 and k=0.005-0.03. The micro-hardness is between 75-85 GPa, i.e. typical for diamond films. Diamond is an ideal coating in optical applications in harsh environments; it is chemically inert, strong, and broad band optically transparent. An important quality for a diamond optical coating is surface smoothness. NCD can be fabricated with great precision with excellent optical and mechanical properties that retains the attractive physico-chemical properties of diamond. A NCD surface is characterized by a large surface area due to the nanocrystalline structure. For the same reason the NCD surface contains a large number of low-coordinated carbon atoms that may form bonds to a large number of molecules. In fact, a major advantage with a NCD surface is that it can be manipulated in several ways to covalently bind a number of molecules (ligands) via e.g. amine, carboxyl and thiol coupling directly to or via linkers low-coordinated C atoms. Methods to functionalize NCD include for example: i) Direct chemical methods applied on NCD involving fluorination, organic free radical additions and fluorine displacement [15]; ii) Inducing hydrogen termination on the NCD for an example by exposing NCD surface with hydrogen atoms for 30 min at 700° C. [16]; iii) Electrochemical attachment schemes for binding of nitrophenyl linker to the H- or O-terminated diamond [1]; iv) Photochemical immobilization on H-terminated NCD [1; 16; 17]; v) Direct chemical reaction between NCD surface and radio-frequency plasma induced gas radicals [18; 19]. It has recently been shown that NCD can be used as an electrochemical biosensing surface [16]. The combination of its advantageous mechanical, chemical and physical properties makes NCD an ideal biosensor which is biocompatible and does not bio-degrade. The simultaneous broad band waveguiding properties, the intrinsic narrow band emission properties, the microfabrication and miniaturization properties, mechanical and chemical stability, surface functionalization properties, and biocompatibility makes NCD an attractive candidate material for remote, wireless, high-throughput in vivo diagnosis.

Of special interest is the surface and interface analysis made possible with ATR-IR where the solid IRE surface has been functionalized. In this manner the IRE is made an integral part of the measurement system. ATR-IR has been used in biosensing [11; 12], antibody recognition [20], in situ monitoring of bilayer formation [21], surface concentration determination [12; 20; 22], detection of protein conformational change upon adsorption or molecular interaction [23; 24], protein secondary structure determination [22; 25], and orientation in proteins and lipids [22; 26]. Recently some progress has also been made to functionalise IREs with crystals based on germanium [12; 20; 27] and silicon [11; 28]. An appropriately functionalised IRE can be used as a biosensor, for example, or for protein fishing. However, it is still a challenge to achieve a versatile sensing device based on ATR-FTIR spectroscopy. The major obstacle to overcome is to appropriately functionalise the IRE. Currently, commercially available IREs are not prepared for this; they are integrated within a complete ATR-FTIR accessory, which is mounted in a spectrometer. Due to their high cost, regeneration of the surfaces is of high priority. Moreover, when building up a functionalised IRE surface in a layer-by-layer fashion, for example, for immobilising peptides or other biomolecules, it is essential to optimise each step and test the functionality as well. Very recently, we have demonstrated a novel approach towards an in situ biosensing method based on ATR-FTIR spectroscopy with exchangeable functionalised sensor chips based on "upside-down" ATR measurements of ex situ prepared chips pressed onto a IRE by an anvil-type piston press [29]. None of these studies use NCD as detection or transducer material.

Mid-IR waveguides have attracted attention because of its use as remote chemical sensors or small volume samples chemical analysis. A mid-IR waveguides can be thought of as a miniaturized MRE wherein the light undergoes multiple internal reflections between media of different refractive indices and where the thickness or diameter of the waveguide is not too large in comparison with the wavelength of the propagating light. Mid-IR waveguides are characterized by multiple internal reflections that yield an interference pattern in the measured single beam intensity corresponding to the standing wave mode structure predicted by waveguide theory. Previous reports have shown the potential of surface enhanced infrared absorption in planar silver halide fibers [30], tapered mid-IR Ge elements [31; 32] and integrated Si optical waveguides [7; 8]. It is non-trivial to manufacture free-standing IR fiber waveguides and thus supported thin planar waveguides provide an interesting option to make IR waveguides for EWS applications. In contrast to the visible light region, where many suitable materials are commercially available and easy to manipulate, there are hitherto few options for appropriate IR-transmitting materials with high refractive index, low power attenuation, mechanical strength and chemical inertness. To the best of our knowledge we are only aware of three reports in the literature of mid-infrared planar waveguides. Two of them utilize monochromatic light [33], while the other uses broad band light focused into a hand-grinded 30 and 50 µm thick planar Ge waveguide employing a commercial IR microscope assembly [31]. None of these reports use diamond or NCD as waveguide material or as component in the waveguide.

DESCRIPTION OF THE INVENTION

The object of the invention is to provide a new optical sensor unit for evanescence wave spectroscopy, which sensor unit overcomes one or more drawbacks of the prior art. This is achieved by the sensor unit as defined in the independent claims.

According to one aspect of the invention there is provided an optical sensor unit for infrared evanescence wave spectroscopy (IR-EWS) analysis of chemical and biological substances in an analyte, comprising a waveguide with a sensor surface to be put into contact with the analyte, wherein the sensor surface is provided with an affinity enhancing layer. According to specific aspects, the affinity enhancing layer may be comprised of nano-crystalline diamond (NCD), the waveguide and the sensor surface may be integrally formed of NCD, the waveguide may be comprised of a material other than NCD with a refractive index above 2 with respect to light in the infrared range, and that the sensor surface is comprised of a NCD film deposited on the wave guide. According to a specific aspect the waveguide may be comprised of a material selected from the group of: Ge, diamond, Si, silver halide, InGaSb, and chalcogenide. According to a further aspect, the waveguide may be thin enough to achieve standing waves when coupling in at the spectroscopic wavelengths. According to a further aspect, the optical sensor unit according may comprise an in-coupling element and an out-coupling element, wherein at least one of said elements is integrated with the waveguide.

According to a further aspect, the optical sensor unit may comprise a substrate member with at least one waveguide formed at a first surface thereof, and wherein the sensor surface of the waveguide is exposed in an associated recess formed in the opposite substrate surface, specifically, the substrate may be a silicon wafer, the waveguide may be comprised of diamond that is deposited on an intermediate cladding layer on the first substrate surface.

There further provided an infrared evanescence wave spectroscopy system comprising an optical sensor unit according above.

There further provided an optical sensor unit for evanescence wave spectroscopy (EWS) analysis of chemical and biological substances in an analyte, comprising a waveguide with a sensor surface to be put into contact with the analyte, wherein the waveguide is comprised of diamond.

There further provided an internal reflection element (IRE) for attenuated total reflection (ATR) infrared spectroscopy analysis of chemical and biological substances in an analyte, comprising a sensor surface to be put into contact with the analyte, wherein the sensor surface of the waveguide is comprised of nano-crystalline diamond (NCD).

Herein we describe various aspects and embodiments of the invention related to a method and device for analysis of chemical of biological substances, in particular using an infrared light waveguide made of nanocrystalline diamond (NCD) or coated with a thin layer of NCD on polycrystalline diamond. The materials, methods and light propagation geometry are chosen so that the combination yields high transmission, favorable analysis condition and versatile surface chemical functionalization properties to achieve high selectivity, sensitivity, and throughput analysis as well as easy-to-use and reproducible operation. According to one embodiment, the waveguide comprises NCD, preferably NCD with diamond-like properties, in particular NCD with diamond-like broad band transmission properties. The waveguide may either be comprised of pure NCD or a NCD film which is coated onto a high-refractive index infrared material, such as Ge, diamond, Si, silver halide, InGaSb, and chalcogenide, capable of narrow or broad band transmission of light, in particular infrared light. According to one embodiment, the NCD film is coated on intermediate layers with intermediate refractive index between the waveguide and the NCD film to ensure simultaneous efficient light coupling and beneficial bonding properties between the NCD film, underlying layers and waveguide materials, which ensures mechanical stability and avoids chemical mixing (diffusion) of elements between the films. According to one particular embodiment, the NCD film is coated directly onto diamond, preferably high grade IR optical quality diamond, and in particular high grade mid-IR optical quality diamond.

The waveguide may be a free-standing device or be supported on a substrate material which may contain additional films or cladding layers with low refractive index compared to the waveguide (e.g. $SiO_2$, MgO, alkali halide, alkaline rare earth halide or oxide, $Al_2O_3$, chalcogenide, nitrides, or combinations or dopant modified combinations of these depending on waveguide materials) that reduces absorption losses of the transmitted infrared light. The thickness or diameter of the waveguide is preferably thin enough to yield an interference pattern in the measured single beam intensity corresponding to the standing wave mode structure predicted by waveguide theory, in order to yield strong enhancement of the measured sensitivity of the device. The dimension of the waveguide is typically of the order of 1-100 micrometer, and typically 5-30 micrometer for IR waveguiding. The length of the waveguide should be made such that the attenuation coefficient (in units of $mm^{-1}$) is less than 1, preferably less than 0.5, and in particular less than 0.3 in the wavelength region of interest for EWS. The waveguide geometry and light beam focusing assembly is made such that it transmits light, preferably infrared light, and in particular mid-IR light, with large propagation angle, $\theta_1$, inside the waveguide to achieve multiple internal reflections at the interfaces surrounding the waveguide. The light propagation properties thus obtained are optimized to achieve high sensitivity for EWS of chemical and biological substances adsorbed at the interface of the NCD waveguide device, preferably for IR light and in particular for mid-IR light. In case of intrinsically generated light within a doped diamond waveguide the light, preferably near-IR, visible or ultraviolet light, and in particular visible light, is further transmitted through the waveguide and by the same principles as described above, which allows for EWS analysis of chemical and biological substances on the NCD surface, which may or may not be modified with a NCD film.

According to one embodiment an evanescence wave spectroscopy system comprises a broad band infrared light source or a monochromatic light source, preferably an IR light source, and in a particular a mid-IR light source. Alternatively there is provided a method and device where a NCD waveguide structure is modified by color centers (such as N—V, Ni—N) or to produce narrow band emission of light including ultraviolet, visible and IR light within the waveguide instead of or in combination with directing light from an external light source.

In case of an external light source it is essential that the sensor unit or the system comprises efficient optical elements for focusing the light into the waveguide (light transmitting objective lens), preferably for IR light and in particular for mid-IR light. According to one embodiment, it comprises a smooth entrance surface for the light with root means square roughness much less than the wavelength of the light that hence reduces light scattering, that is less than 3 micrometers, preferably less than 1 micrometer, and in particular less than 0.5 micrometers. The beveling surface (bevel angle is between 0 and 90 degrees) of the waveguide are preferably either directly fabricated with focused ion beam milling or laser ablation. The bevel surface can also be fabricated with for instance gray scale lithography, hot embossing or nano imprint lithography in a polymer layer deposited on the waveguide, followed by a transfer of the beveled polymer surface into the waveguide material by plasma etching. The focusing element can be an external unit or integrated with the waveguide. The invention contains methods to fabricate an integrated in-coupling element with a waveguide. The element which will collect light into the waveguide can for instance be realized either as a focusing lens or as a diffractive grating. Methods to fabricate these elements can be electron-beam lithography, photolithography, plasma dry etching, laser ablation, focused ion beam etching or gray-scale lithography. In particular, the device may be designed and fabricated to enable insertion of the NCD waveguide structure in conventional ATR accessories.

According to one embodiment, the device comprises efficient light collecting optics (light transmitting condensing lens), preferably for IR light, and in particular for mid-IR light. It contains a smooth exit surface for the light with root means square roughness much less than the wavelength of the light that hence reduces light scattering, that is less than 3 micrometers, preferably less than 1 micrometer, and in particular less than 0.5 micrometers. The beveling surface (bevel angle is between 0 and 90 degrees) of the waveguide are preferably either directly fabricated with focused ion beam milling or laser ablation. The bevel surface can also be fabricated with for instance gray scale lithography, hot embossing or nano imprint lithography in a polymer layer deposited on the waveguide, followed by a transfer of the beveled polymer surface into the waveguide material by plasma etching. The exit surface can be further coated with thin films with intermediate refractive index between the waveguide and the focusing element that increases the transmitted light intensity onto the collecting optical element. The collecting element can be an external device or integrated with the waveguide. The invention contains methods to fabricate an integrated out-coupling element with a waveguide. The element which will collect light from the waveguide can for instance be realized either as a focusing lens or as a diffractive grating. Methods to fabricate these elements can be electron-beam lithography, photolithography, plasma dry etching, focused ion beam etching, laser ablation or gray-scale lithography. In particular, the device may be designed and fabricated to enable insertion of the NCD waveguide structure in conventional ATR accessories.

The device contains an efficient light detector, preferably an IR detector and in particular a mid-IR detector.

There is further provided methods to functionalize the NCD film and to utilize the exposed high surface area of the NCD film to a medium for improved selectivity and sensitivity by EWS. In particular it is described how the device enables sensitive, selective and quantitative EWS analysis of chemical or biological species in the medium in which the device is immersed by adding an immobilization or affinity layer onto the NCD coating to selectively bind chemical or biological substances. The NCD coated waveguide surface provides various ways of anchoring recognition layers to achieve optimal specific binding capacity with analytes of interest. By direct coupling methods or via H-terminated NCD surfaces it is possible to build up, step-by-step, layers containing end groups of carboxyls, amines, thiols, etc., which act as binding points for macromolecules as enzymes, proteins, oligonucleotides, carbohydrates or for other organic species containing recognition sites. Upon binding event EW absorption (infrared light) or fluorescence (UV-vis light) spectra are generated from which several binding characteristics can be extracted such as: 1) Distinguish between specific and unspecific bonds, 2) Molecular information on binding modes, 3) Saturation surface coverage. 4) Bond strengths between interacting species, and 5) Binding kinetics. This device has potential for applications in areas of environmental science (also in harsh conditions), chemical and biological sensing, and medical aspects of sensing in vitro or in vivo due to the biocompatibility of diamond.

Other EWS applications of the NCD waveguide include quality control of solids and liquids (water cleaning, food and drug industry, etc) where adsorption directly on the NCD surface (without functionalization) can be used and is associated with well-resolved intense vibrational or fluorescence spectra from which material quality information is gained. If spectral information is complex these measurements can be applied in conjunction with multivariate data analyses. Levels of pureness can be determined and eventual impurities can be identified.

BRIEF DESCRIPTION OF THE DRAWINGS

The invention will be described in detail below with reference to the drawings, in which

FIGS. 11a (angle of incidence) and 11b (bevel angle)), with refractive index n=1.5 (water; FIGS. 11c (angle of incidence) and 11d (bevel angle)) and n=2.0 (high-index material; FIGS. 11e (angle of incidence) and 11f (bevel angle)).

FIG. 14 shows a scheme that exemplifies the functionalization of a waveguide or IRE coated with an affinity layer for EWS for detection of chemical or biological substances. (1) The infrared light experiences standing wave propagation, single or multiple reflections within the waveguide/IRE, (2) The waveguide/IRE is coated with a thin affinity layer such as NCD film which facilitates EWS on the interface between the affinity layer and the surrounding medium, (3) the NCD film is functionalized by adding an immobilization layer (affinity layer) which is conjugated to the low-coordinated C atoms in the NCD film, and (4) The immobilization layer consists of recognition molecules that selectively bind chemical or biological substances present in the solution or gas phase which the device is immersed in.

DETAILED DESCRIPTION OF EMBODIMENTS

According to one embodiment there is provided a method and device for analysis of chemical of biological substances is described using a light waveguide made of nanocrystalline diamond (NCD) or with NCD applied as thin coating on a waveguide. In particular, an optical sensor unit for evanescence wave spectroscopy (EWS) analysis of chemical and biological substances in an analyte, comprising a broad band infrared (IR) waveguide or internal reflection element is described. The materials, methods and light propagation geometry are chosen so that the combination yields high transmission, favorable analysis condition and versatile surface chemical functionalization properties to achieve high selectivity, sensitivity, and throughput analysis as well as easy-to-use and reproducible operation. The device comprises, according to one embodiment of the invention, a NCD film coated onto a high-refractive index infrared materials capable of broad band transmission of light, in particular IR light. Further it comprises a light source, in particular a broad band mid-IR and near-IR light sources, a suitable device that efficiently focus the IR light into the waveguide, a suitable geometry such as a planar waveguide geometry with entrance and exit surfaces with root means square roughness much less than the wavelength of the light that reduces light scattering and efficiently couple the focused light into and out from the waveguide. The device has efficient light collecting optics, and an efficient IR light detector, in particular a mid-infrared detector. The waveguide may be a free-standing device or be supported on a substrate material which may contain additional films or cladding layers with low refractive index compared to the waveguide that reduces absorption losses of the transmitted infrared light. The thickness or diameter of the waveguide is thin enough to yield an interference pattern in the measured single beam intensity corresponding to the standing wave mode structure predicted by waveguide theory, in order to achieve multiple reflections of the light in the waveguide and thus enhance the sensitivity of the device for evanescence wave spectroscopy analysis of chemical and biological substances. Further, the waveguide geometry and light beam focusing assembly is made such that it transmits light with large propagation angle inside the waveguide; here we show results with up to 62 degrees in a diamond waveguide. There is further provided methods to functionalize the NCD film with organic layers and to utilize the exposed high surface area of the NCD film to a medium for improved selectivity and sensitivity. In particular it is described how the device enables detailed analysis and quantification of unknown chemical, biological or medical active species in the medium in which the device is immersed by adding an immobilization layer onto the NCD coating to selectively bind unknown chemical or biological substances.

Figure 1:
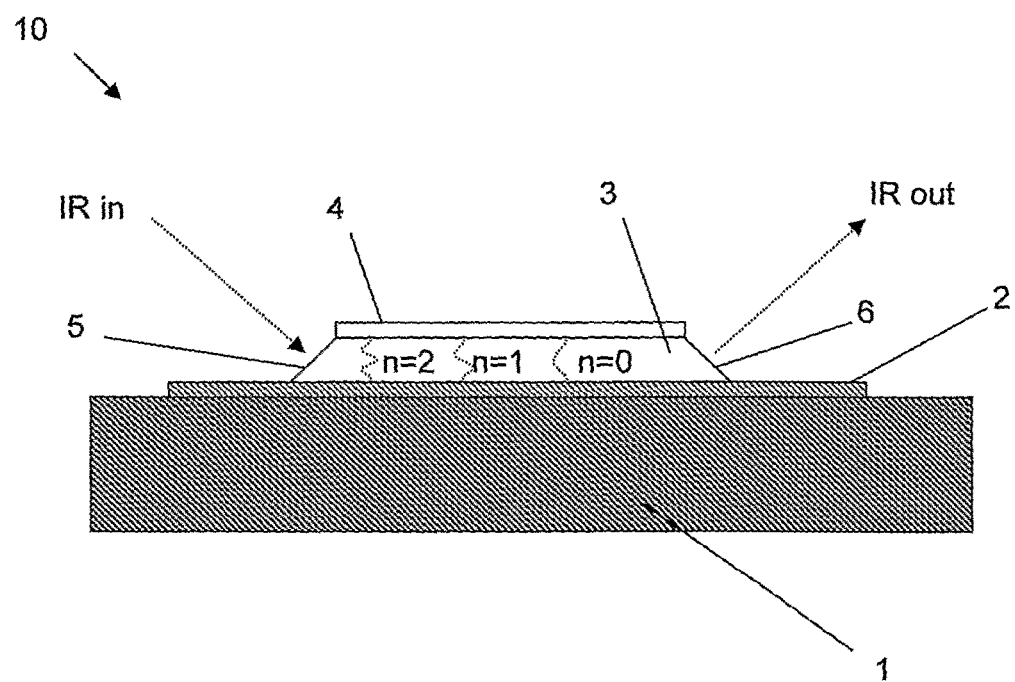
FIG. 1 shows a schematic illustration depicting the principle of a waveguide device according to one embodiment (not proportional to actual dimensions). The first three standing wave modes (n=0, 1 and 2) are indicated in the figure.

FIG. 1 shows a schematic illustration depicting the principle of a waveguide device 10 according to one embodiment (not proportional to actual dimensions). The reference numbers in the figure refer to substrate material 1, cladding layer 2 with refractive index much smaller than the waveguide, a thin affinity enhancing layer 4, e.g. a NCD film, coated on a waveguide 3 with high-refractive index, where the latter determines the propagation properties of the light inside the waveguide 3, and the substance under investigation. The waveguide 3 is provided with an entrance surface 5 for receiving IR light from a light source and an exit surface 6. As is schematically indicated in FIG. 1 the thickness of the waveguide is selected thin enough to yield an interference pattern in the measured single beam intensity corresponding to the standing wave mode, illustrated by n=0 to 2 in FIG. 1, structure predicted by waveguide theory, in order to yield strong enhancement of the measured sensitivity of the device. The dimension of the waveguide is typically of the order of 1-100 micrometer, and e.g. 5-30 micrometer for IR waveguiding. The length of the waveguide should be made such that the attenuation coefficient (in units of $mm^{-1}$) is less than 1, preferably less than 0.5, and in particular less than 0.3 in the wavelength region of interest for EWS. The waveguide geometry and light beam focusing assembly is made such that it transmits light, preferably infrared light, and in particular mid-IR light, with large propagation angle, $\theta_1$, inside the waveguide to achieve multiple internal reflections at the interfaces surrounding the waveguide.

Figure 2:
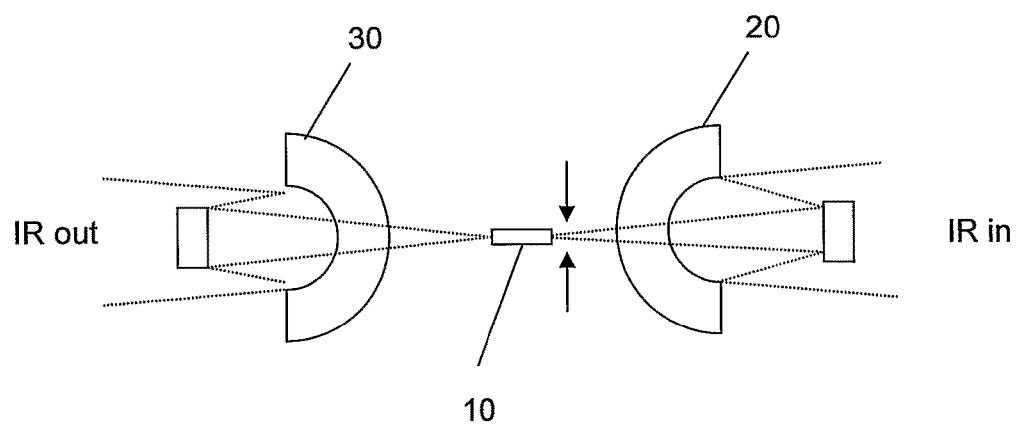
FIG. 2 shows an IR light beam focusing and collecting device together with an illustration of its function.

FIG. 2 shows a schematic embodiment of an IR light beam focusing 20 and collecting 30 arrangements together with an illustration of its function. The focusing element 20 can be an external unit or integrated with the waveguide. The invention contains methods to fabricate an integrated in-coupling element with a waveguide. The element which will collect light into the waveguide can for instance be realized either as a focusing lens or as a diffractive grating. Methods to fabricate these elements can be electron-beam lithography, photolithography, plasma dry etching, laser ablation, focused ion beam etching or gray-scale lithography. In particular, the device may be designed and fabricated to enable insertion of the NCD waveguide structure in conventional ATR accessories. The collecting element 30 can be an external device or integrated with the waveguide. The invention contains methods to fabricate an integrated out-coupling element with a waveguide. The element which will collect light from the waveguide can for instance be realized either as a focusing lens or as a diffractive grating. Methods to fabricate these elements can be electron-beam lithography, photolithography, plasma dry etching, focused ion beam etching, laser ablation or gray-scale lithography. In particular, the device may be designed and fabricated to enable insertion of the NCD waveguide structure in conventional ATR accessories.

Figure 3:
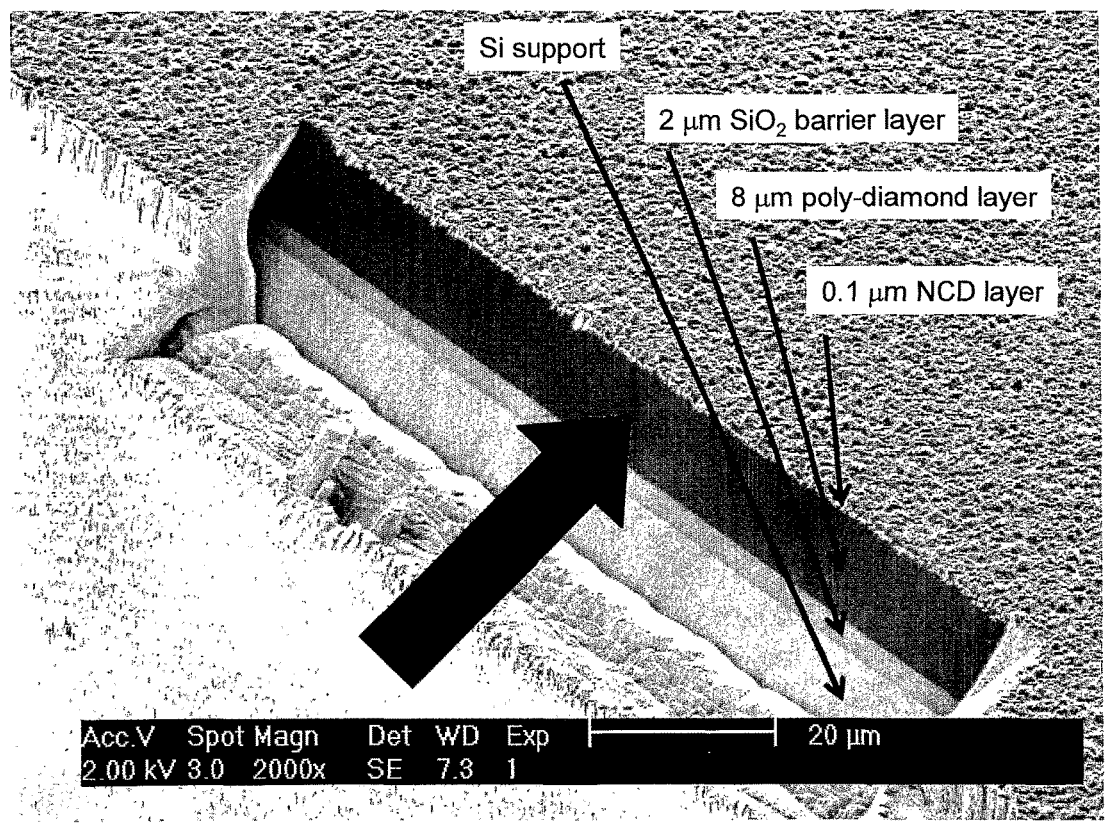
FIG. 3 shows a SEM image of a microfabricated planar NCD coated poly-crystalline diamond waveguide on a $SiO_2$/Si substrate.

FIG. 3 shows a SEM image of a microfabricated planar NCD coated poly-crystalline diamond waveguide 10. The microfabricated planar NCD coated poly-crystalline diamond waveguide has the dimensions 2 mm×3 mm×8 μm and is grown on a 2 μm thick $SiO_2$ film on a Si substrate. (Below) The entrance 5 and exit surfaces (not shown) are polished/microstructured with FIB. The inset of the fabricated entrance surface is not shown, but it may be similar as the exit surface.

Figure 4A:
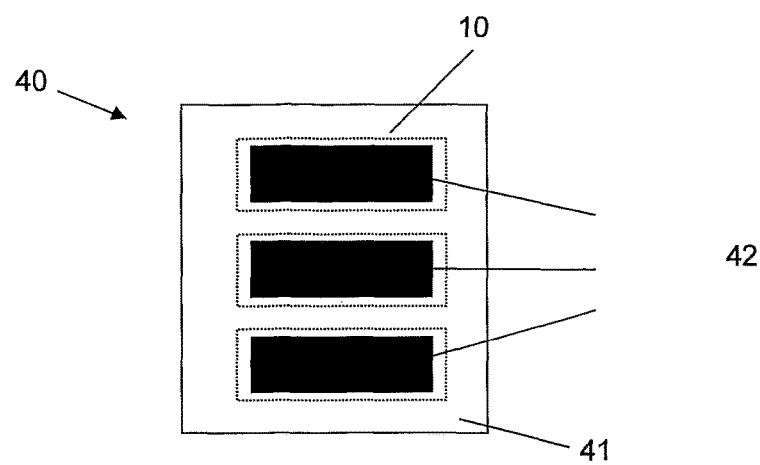
FIGS. 4a and 4b schematically show top and cross-section views, respectively, of a micro fabricated waveguide well structure appropriate for liquid analysis which may comprise several waveguides on the same chip.
Figure 4B:
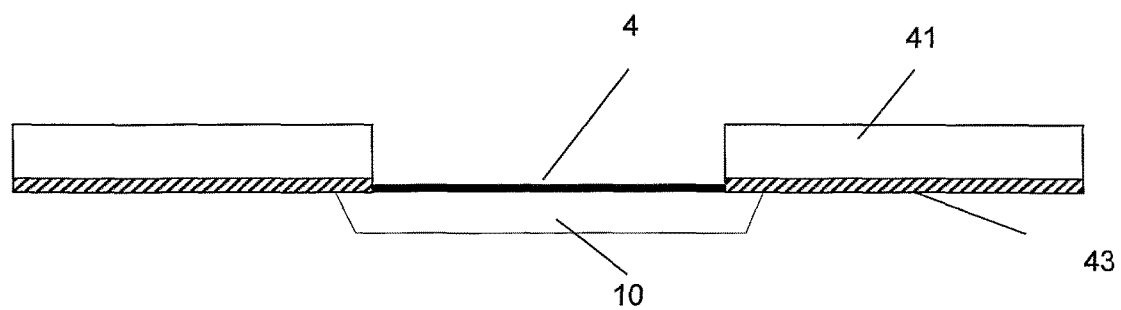

FIGS. 4a and 4b schematically show a microfabricated waveguide well structure 40 appropriate for liquid analysis which may comprise several waveguides 10 on the same chip. In FIG. 4a the waveguides 10 are shown as dotted outlines, as they are arranged at the back side of the substrate. FIG. 4a is a top view of a flat substrate 41 with three sensor wells or recesses 42. The number of sensor wells may be varied with respect to the type of analysis that is to be performed, and due to the microfabrication process and the sizes involved, a very large number of sensor wells may be provided on a single substrate. Moreover, the microfabrication process may permit forming of other microstructures on the same substrate, such as microfluidic conduits and components that may be used for supplying analyte to the sensor wells. Moreover, as is discussed above the microfabrication process may also be used to form optical components other than the waveguides, e.g. in or out coupling elements.

FIG. 4b shows a schematic cross section of the microfabricated waveguide well structure 40 through one sensor well 42. The substrate 41 may e.g. be a silicone wafer, and in order to achieve enhanced wave guide properties, a cladding layer 43 of low refractive index is arranged intermediate the substrate 41 and the waveguide 10. In this embodiment, the sensor surface is arranged on the substrate side of the wave guide 10 and is exposed by an associated well or recess through the substrate. As discussed more in detail above, the sensor surface is provided with an affinity enhancing layer, e.g. NCD.

The substrate of the microfabricated waveguide well structure 40 effectively separates the sensor side of the waveguide that is to be put into contact with the analyte, e.g. a liquid sample, from the optical side.

According to one embodiment, the microfabricated waveguide well structure 40 is produced by the steps:
  depositing an optical cladding layer on a first surface of a substrate,
  depositing at least one diamond wave guide on the first surface,
  forming a recess/well associated with each diamond wave guide in the second, opposite, surface of the substrate through the cladding layer, to expose a section of the diamond wave guide surface from said second side, and
  depositing an affinity enhancing layer on the exposed section of the diamond waveguide forming a sensor surface.

The various steps may be performed using any suitable microfabrication techniques available, such as discussed above, and in the following examples.

Figure 15:
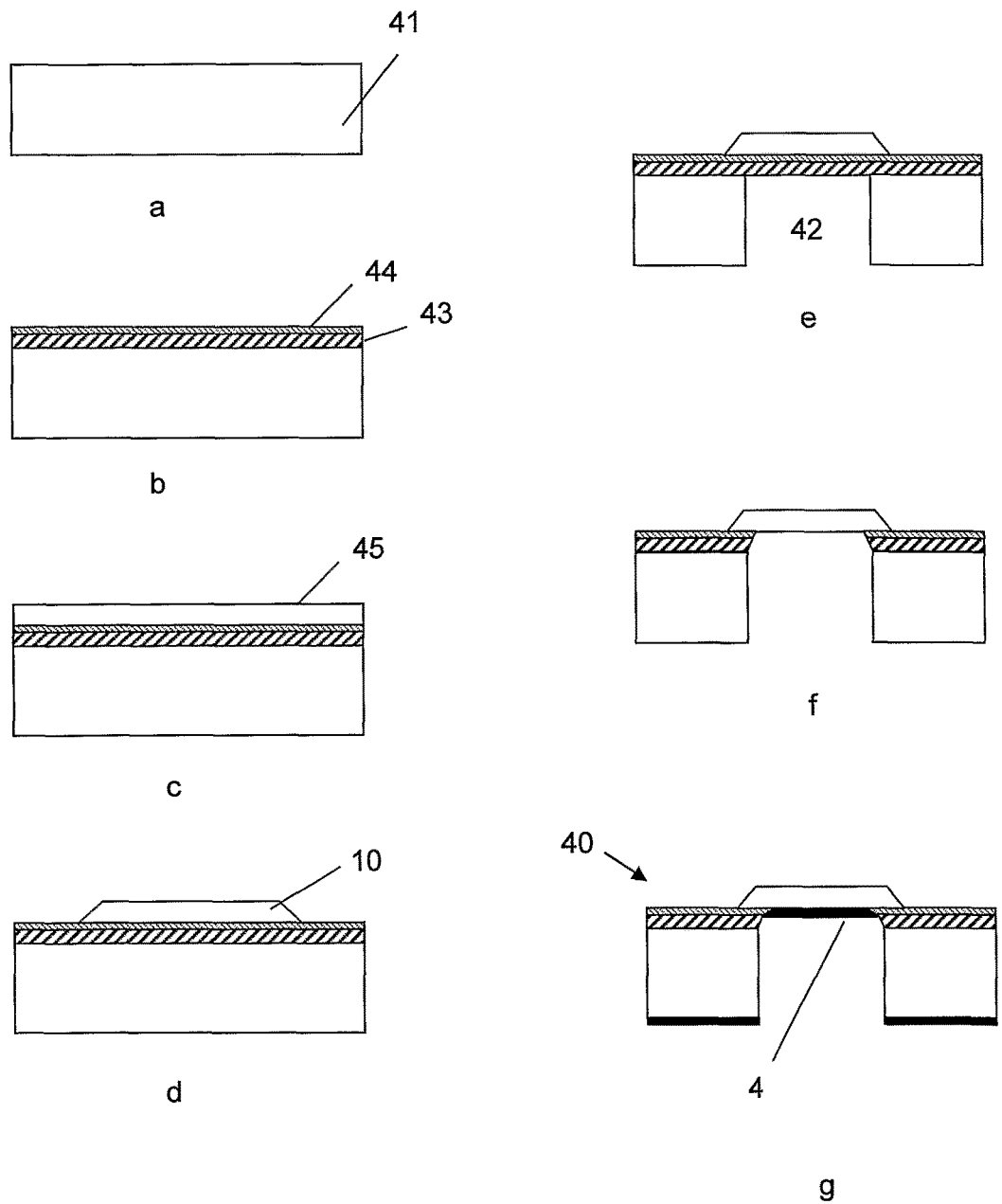
FIG. 15. Schematic drawings illustration the sequence of steps involved in microfabrication of a NCD coated diamond waveguide well structure as depicted in FIG. 4.

In more details, and as is illustrated in FIGS. 15 a-g, the waveguide well structure can e.g. be made in the following way. A silicon substrate 41 is coated on a first surface thereof with 2 μm thick cladding layer 43 of e.g. silicon oxide by chemical vapour deposition (FIG. 15b). To enhance the adhesion of the wave guiding diamond layer a thin adhesion layer 44 e.g. of silicon nitride (200 nm thick) is deposited by low pressure chemical vapour deposition (LPCVD). A 30 μm thick wave guide layer 45 of polycrystalline diamond is then deposited on the silicon nitride by microwave plasma chemical vapour deposition (FIG. 15c). The diamond layer 10 is then polished to a surface roughness below 100 nm root-mean square (not shown). The diamond layer 10 is then sputter coated with a 2 μm thick aluminium (Al) layer (not shown). By e.g. standard photolithography both waveguide structures and alignment markers are defined in the Al layer (not shown). The waveguide structures 10 (and the alignment structures) are then transferred to the diamond layer by inductively coupled plasma etching in oxygen/argon chemistry (FIG. 15d). The Al layer is not etched in this chemistry. This is followed by lithographic patterning of well structures 42 on the second opposite surface of the silicon substrate 41. Again Al is deposited with sputtering, used as a protective layer during the plasma etching step (not shown). The well structures are aligned to the alignment markers on the other side by a double sided mask aligner (not shown). The well 42 is then plasma etched down to the cladding layer using so called silicon deep reactive ion etching (fluorine chemistry) (FIG. 15e). The cladding layer act as a etch stop layer. By using either plasma etching ($CHF_3$ and $SF_6$ based chemistry) or a combination of hydrofluoric acid wet chemistry (HF, water and buffered HF) the cladding layer is removed in the well 42 so that the polycrystalline diamond film is exposed (FIG. 15f). After these process steps is the remaining photoresist on both sides of the substrate stripped in acetone followed by Al stripping with a standard Al wet etch (phosphoric acid, water, acetic acid, nitric acid). Finally the exposed polycrystalline diamond at the bottom of the wells is coated with a thin NCD layer by e.g. hot filament vapour deposition (FIG. 15g).

Figure 5:
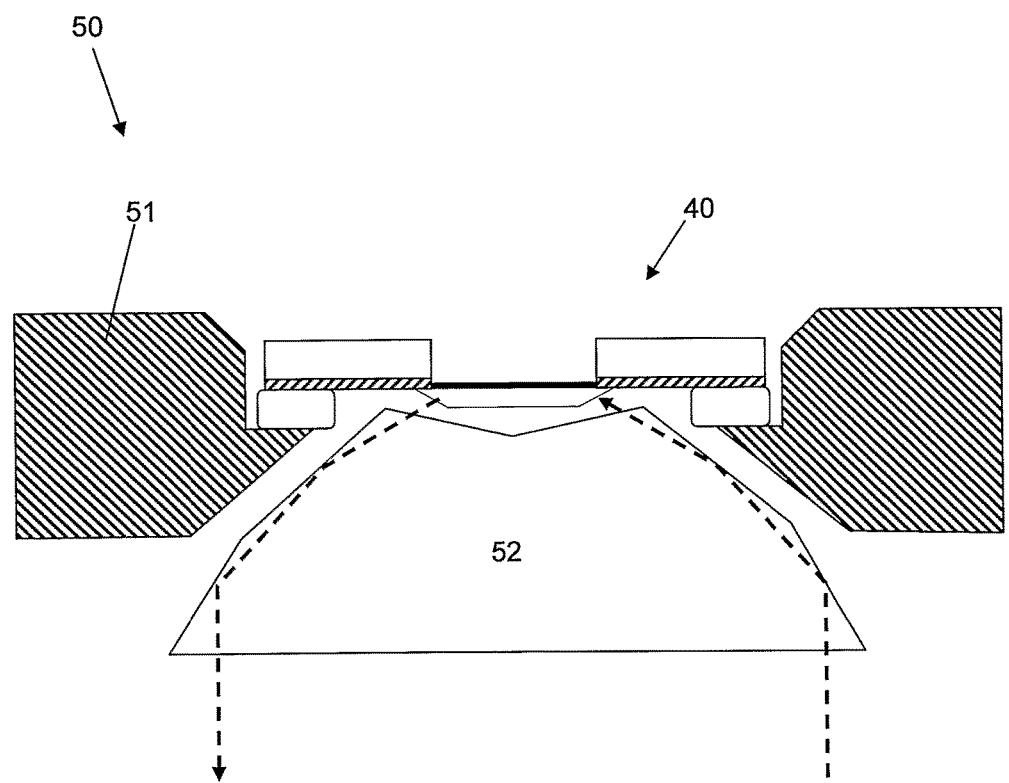
FIG. 5 shows an NCD coated waveguide structure attached onto conventional IR optical elements in an ATR accessory.

FIG. 5 schematically shows microfabricated waveguide well structure 40 arranged in a chip holder 51 of one embodiment of an infra red evanescence wave spectroscopy system 50. According to one embodiment, the spectroscopy system 50 may be based on a conventional ATR spectroscopy system. The spectroscopy system 50 comprises an IR light source (not shown) that emits IR light as indicated by dashed ray in the figure, and one or more IR optical elements 52 including joining elements to the waveguide 40 that focuses and directs the IR light onto the entrance surface of the waveguide 10 and collects light that exits from the exit surface.

Various aspects of the invention will now be illustrated by the following non-limiting examples.

EXAMPLES

Example 1: Nanocrystalline diamond films were grown by a hot-wire CVD method from a $CH_4/H_2$ mixture [16]. The crystal size is in the nanometer range in agreement with our independent results from the Raman measurements presented above. Based on the optical characterization, NCD film growth limitations, our theoretical results, a final waveguide design included a 2 μm thick $SiO_2$ layer grown by oxidation in wet atmosphere at 1050 degrees Celsius of the silicon substrate. The diamond waveguide was constructed from a 10 μm thick poly-crystalline diamond film of infrared optical quality grown on top of the $SiO_2$/Si substrate with an additional thin (0.1 μm) NCD layer grown on the polycrystalline diamond film. We use polycrystalline diamond as waveguide and grow NCD on top of the poly-crystalline film rather than having a thick NCD film. The reason for this is mainly because the poly-crystalline diamonds has in general superior optical properties and scatter less light than NCD films. With poly-crystalline diamond, it is also straightforward to grow a mechanically stable NCD film with good substrate adherence. The poly-crystalline diamond was also grown using hot-wire CVD from $CH_4/H_2$ mixture (but at other ratios compared to deposition of NCD). To reduce the effect standing wave interference (beat pattern) [31], a bevel angle in the range 10-45 degrees was chosen, which yields a deconstructive wave mixing for unpolarized light.

The lithographic fabrication of the NCD waveguide is as follows: After cleaning the wafer stack (Si/$SiO_2$/Polycrystalline diamond/NCD) in acids the diamond substrate is sputtered with a 200 nm thick aluminum layer. In a next step a thin layer (1 μm) of photo-resist is spun out on top of the aluminum. After a soft bake on a hot plate the waveguide pattern is transferred to the photoresist with contact lithography followed by resist development and hard bake of the remaining resist. The waveguide pattern in resist is then transferred into the aluminum by dry etching of aluminum. The dry etching uses $Cl_2$ and $BCl_3$ as etch gases and is performed in a commercial inductively coupled plasma (ICP) etching system. To fabricate the diamond waveguides a home built ICP etching system is employed. In earlier research we (Uppsala University/Adamantis) have shown that diamond etching in ICP etching system generates high etch rates and smooth pattern transfer[34]. The etch gases used for diamond etching is $O_2$ and Ar. The Al pattern on the diamond layer serves as an etch stop during the diamond etching. The waveguide pattern is in this way transferred to the NCD/polycrystalline diamond and the etching stop at the $SiO_2$ layer ($O_2$ and Ar do not etch $SiO_2$). After that the aluminum layer is removed in acids, and the template is transferred to the diamond and a resulting diamond waveguide is produced.

To fabricate a bevel angle between 10 and 45 degrees a focused ion beam milling (FIB) system is be used. With this system one can carve in the diamond with high precision in almost any direction. An additional advantage with FIB is that the resulting surface will be smooth and thus reduce scattering losses at the interface. To enhance the etch rate of the diamond waveguide we used water vapor during the milling process. This speeds up the etch rate and yields much smoother surfaces compared to milling with out water vapor. Previous studies employing hand grinding resulted in a very rough surface with poor IR coupling into the waveguide [31].

Example 2: An IR beam focusing and collecting device with beam shaper, and XYZ sample manipulation stage. The device is based on a commercial IR microscope (Bruker Optics) with capacity to compress the beam size diameter from millimeter (the instrumental beam diameter can be varied between 0.5 and 12 mm) to a few micrometers. The infrared light beam from the spectrometer is reflected by a set of flat mirrors and a 15× mirror Cassegrainian objective (NA=0.4) into the 8 micrometer thick waveguide. The throughput is refocused and directed back to the spectrometer detector. The NCD-film is placed on an adjustable sample holder. With knife edge aperture (green in the sketch) the beam shape can be adjusted.

Figure 14:
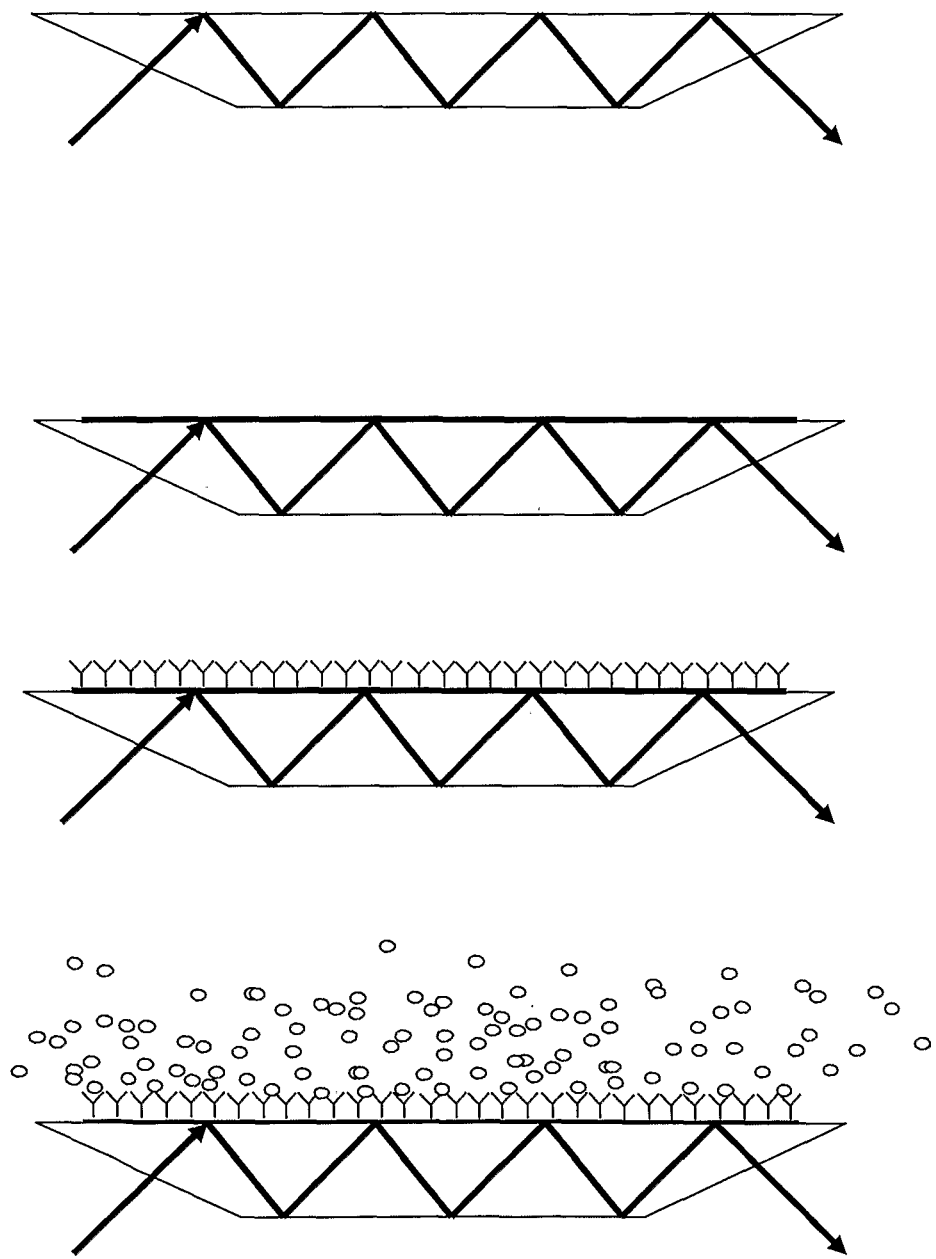

Example 3: A functionalized NCD coated mid-IR waveguide with receptor molecules attached to the surface for selective binding of an analyte (FIG. 14). In FIG. 14 the recognition molecule (receptor) is attached to the solid IRE surface. This is a tedious procedure which commonly implies that the IRE is coated with a thin Si or Au layer (step 2 in FIG. 14). After several subsequent surface chemical treatments the recognition molecule, which is specific to the particular analyte of interest, is anchored to the functionalized IRE surface (step 3 in FIG. 14). This can be done in several ways depending on the application. The recognition molecule can be linked to nanoparticles, polymers, proteins, simple molecules such as sugars, or directly to amide or carboxyl groups. The analyte, which is present in the liquid or gas phase binds (selectively) to the receptor surface and the analyte bonding can be monitored by the spectral changes in the infrared spectrum.

Example 4 gives a theoretical description of a mid-IR diamond waveguide supported on a Si substrate with a thin $SiO_2$ layer grown on top of the Si substrate. We use two different models to describe the waveguide device in FIG. 1: Mode analysis denoted Model 1) and Finite Element Method (FEM) denoted Model 2. The models are used to compute the transmission as a function of dimensions, wavelength and choice of materials. The refractive indices, n, used in the computations (both with Model 1 and Model 2) are as follows: n(Air)=1, n(Si)=3.4, $SiO_2$)=1.46, and n(diamond) =n(NCD)=2.4. Tabulated experimental values of the optical constants for water (n and k) have been used to construct functions that describe their wavelength dependence. We have assumed that Si, $SiO_2$ and the diamond materials are completely lossless (i.e., k=0) in the computations. Thus, intrinsic absorption in these materials is neglected in the computed results. We make no distinction of the optical properties of the diamond waveguide and the NCD film and thus treat both as a single slab demoted "NCD". Model 1 is used to compute the attenuation of individual modes along the waveguide slab. Model 1 is two-dimensional, i.e., we assume that the slab is infinitely wide. The computation is performed in two steps. First, guided modes are computed with simplified boundary conditions, i.e., for a simplified structure consisting of the NCD slab surrounded on one side by $SiO_2$ (infinitely thick) and on the other side by the substance under investigation, but with losses removed. These simplifications are necessary in order to obtain "unperturbed" modes. However, it should be noted that the simplification implies that the reliability of the model decrease with increasing losses of any kind in the actual system. Second, the attenuation of the "unperturbed" guided modes is computed by inserting the real boundary conditions of the structure. On the substrate side the infinitely thick, homogeneous $SiO_2$ material is replaced by a thin (1 μm or 2 μm) $SiO_2$ layer placed on an infinitely thick Si substrate. On the substance side losses are included in the optical properties of the substance under investigation (material 4 in FIG. 6). Thus, we treat the multilayer structure on the substrate side and the losses on the substance side as perturbations to the ideal wave guide system for which the "unperturbed" modes are computed. The power attenuation of the guided wave is described by the attenuation coefficient α as:

$$I(x)=I_0 e^{-\alpha x} \quad (1)$$

where x is the distance along the waveguide, and $I_0$ is power of the guided wave at x=0. For the "unperturbed" modes α=0.

Figure 6:
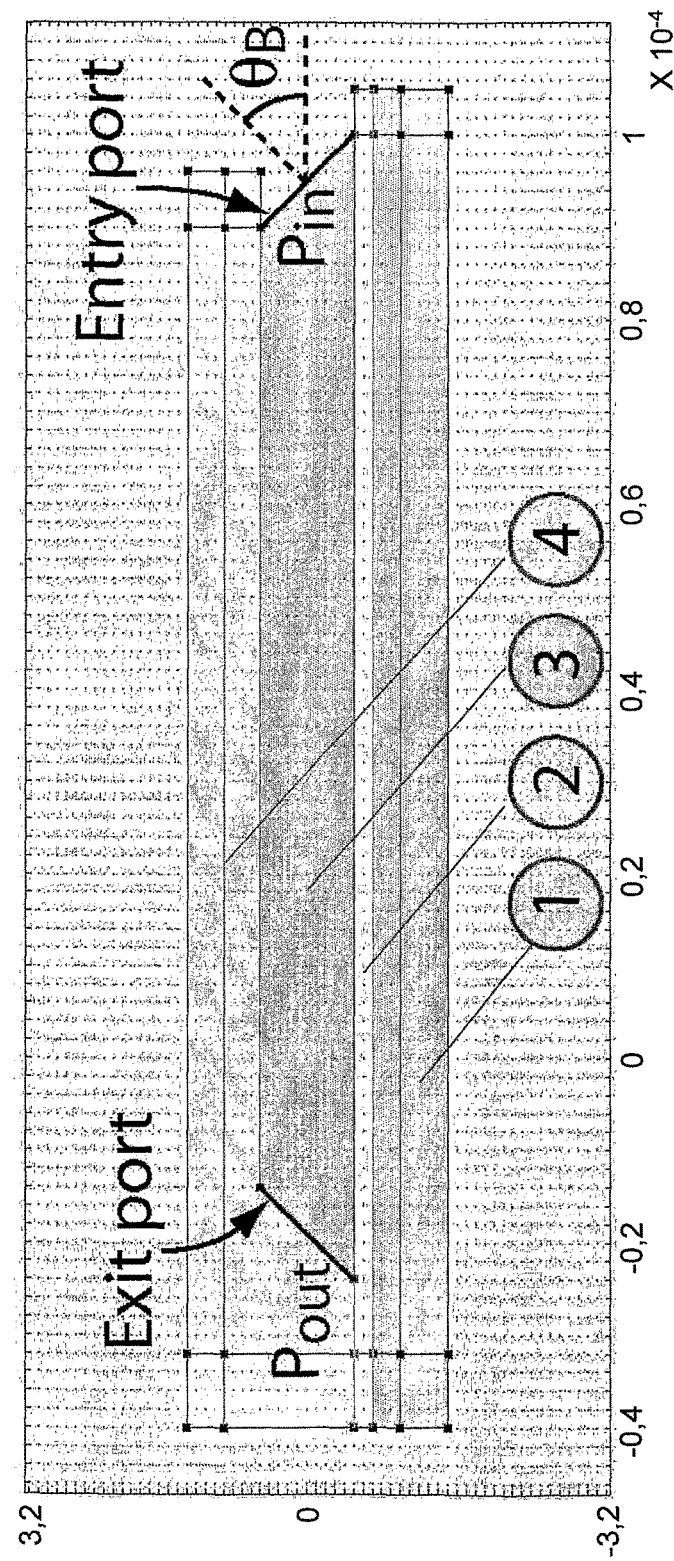
FIG. 6. Geometry of FEM-model used in the calculations of the light propagation in the waveguide. Numbering indicates different materials: 1: Si, 2: $SiO_2$, 3: diamond and 4: air. The diamond waveguide slab is 10 µm thick and 114 µm long. The thickness of the $SiO_2$ layer is 2 µm.

Model 2 is used to compute the transmission of an electromagnetic field through the wave guide, including the effects of slanted entry and exit ports. This model is also two-dimensional. The wave is excited as a plane wave on the entry port. The transmission T is computed from the fraction of electromagnetic power (time average Poynting vector) exiting the wave guide at the exit ports as compared to the power entering the wave guide at the entry port, $T=P_{out}/P_{in}$. The geometry of the FEM-model is shown in FIG. 6. The computations were performed with the COMSOL Multiphysics v. 3.3 software [35]. The number of elements in the mesh was approximately 140000-150000. This means that results for $1/\lambda > 3000$ cm$^{-1}$ are less reliable, since the wavelength must be sufficiently resolved by the mesh.

Figure 7A:
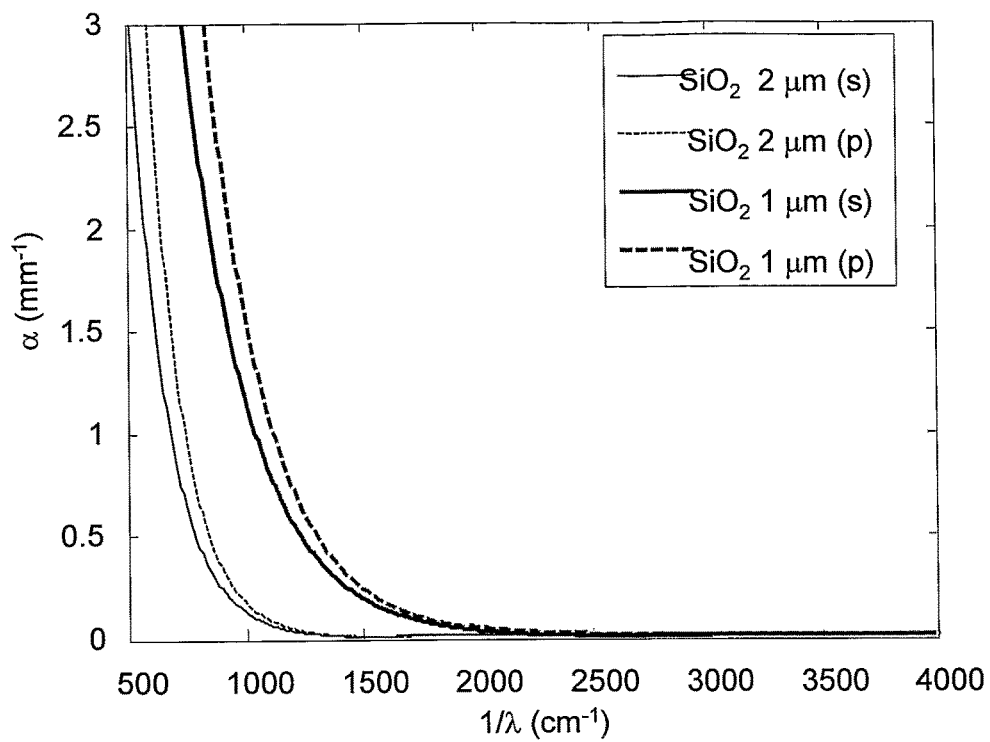
FIG. 7 (a) Attenuation coefficient for mode 0 for the waveguide structure as computed by model 1 using two different $SiO_2$ layer thicknesses 1 µm (thin lines) and 2 µm (thick lines), respectively, and air as the substance under investigation. (b) Transmission (T) versus wave number (1/λ) calculated from the attenuation coefficients in (a) for waveguide length 5 mm. Solid lines indicate s (TE) polarization, and dashed lines indicate p (TM) polarization.
Figure 7B:
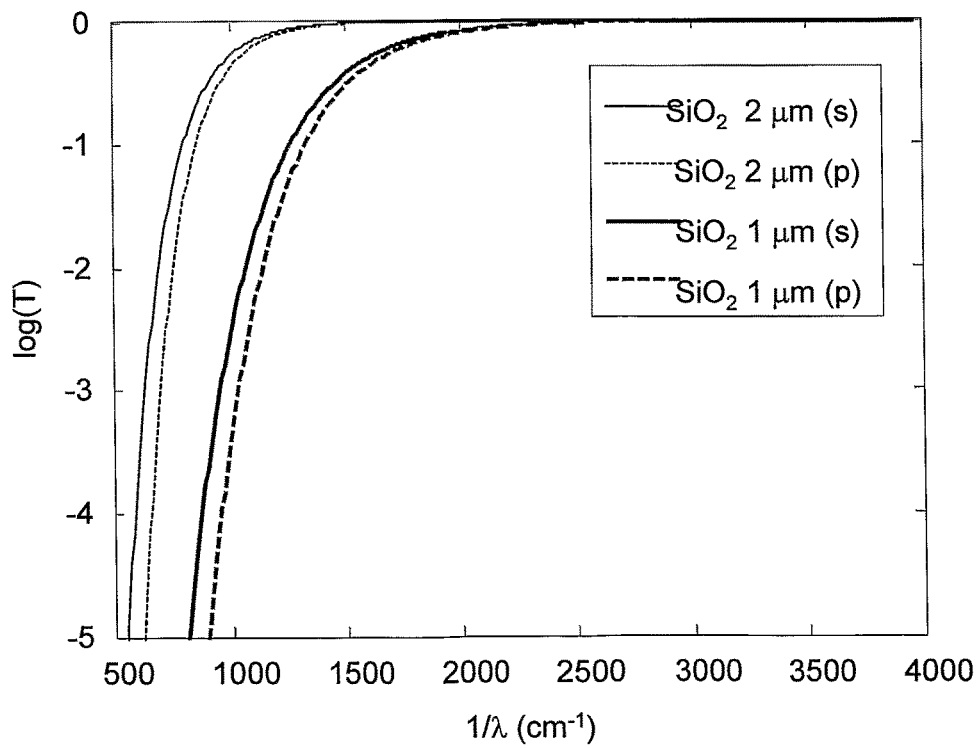

FIG. 7a shows the attenuation coefficient for mode 0 as a function wave number. Two different thicknesses of the $SiO_2$ layer were used, 1 μm and 2 μm (blue and black curves, respectively). The high attenuation at small wave numbers is caused by losses through the $SiO_2$ layer. The result is qualitatively the same also for higher order modes (mode number >0) but with the attenuation extending to larger wave numbers. FIG. 7b shows the corresponding transmission spectra for a 5 mm waveguide. We can conclude from the results in FIGS. 7a and 7b that it is important to make the protective $SiO_2$ layer sufficiently thick in order to have good IR transmission at small wave numbers due to the leakage to the underlying Si substrate.

Figure 8A:
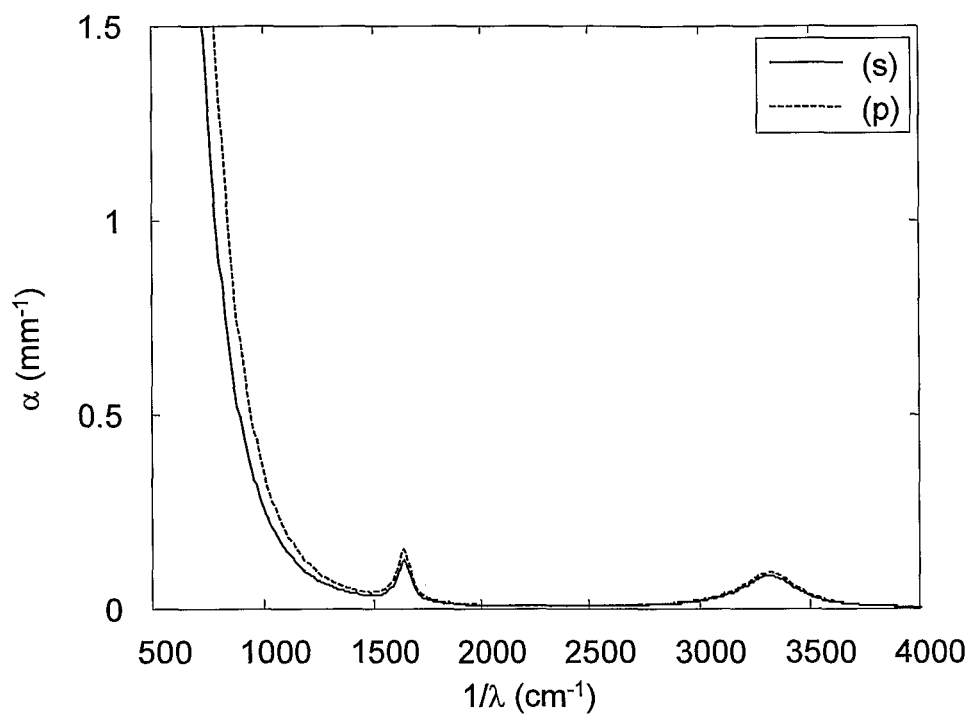
FIG. 8 (a) Attenuation coefficient for mode 0 for the waveguide structure in 4b as computed by model 1 using 2 µm $SiO_2$ film thickness and $H_2O$ as the substance under investigation. (b) Transmission (T) versus wave number (1/λ) calculated from the attenuation coefficient in (a) by using two different waveguide lengths, 5 mm (black lines) and 1 mm (blue lines). Solid lines indicate s (TE) polarization, and dashed lines indicate p (TM) polarization.
Figure 8B:
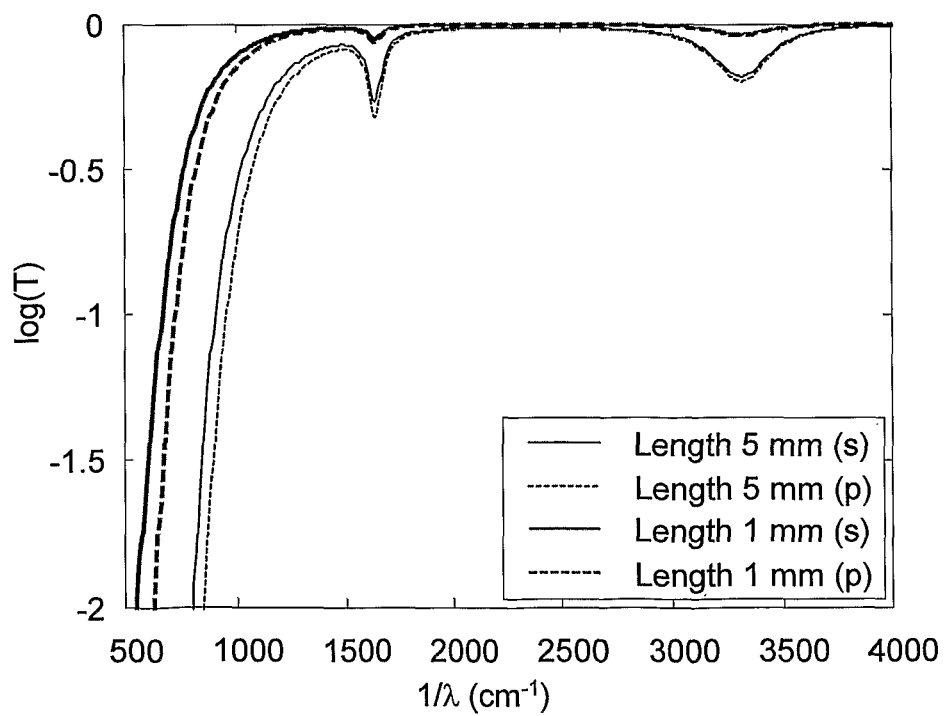

Model 1 was also applied to investigate the dependence of transmission on the length of the waveguide. The results are displayed in FIGS. 8a and 8b. FIG. 8a shows the power attenuation coefficient for the structure in FIG. 6 (with $H_2O$ as the substance under investigation) with $t_{SiO2}$=2 In the small wave number region ($1/\lambda < 1250$ cm$^{-1}$) the wave is attenuated both due to losses in the water and dissipation through the $SiO_2$ layer (see FIGS. 7a and 7b). The vibrational losses due to coupling with the δ(HOH) and ν(OH) modes at ≈1630 cm$^{-1}$ and ≈3330 cm$^{-1}$, respectively are clearly seen. In another example the attenuation coefficient was applied to two different waveguide lengths, 1 mm and 5 mm, respectively. The logarithm of the transmittance represents a linear scaling of the attenuation coefficient with the length of the waveguide. Note that the results in FIGS. 8a and 8b are computed only for mode 0. In a real waveguide there will normally exist several different modes simultaneously, with slightly different attenuation properties. Thus, a real transmission spectrum will depend on all these modes, and the relative strengths of the different modes in the waveguide. Model 1 does not allow the computation of the relative strengths of these modes.

Figure 9:
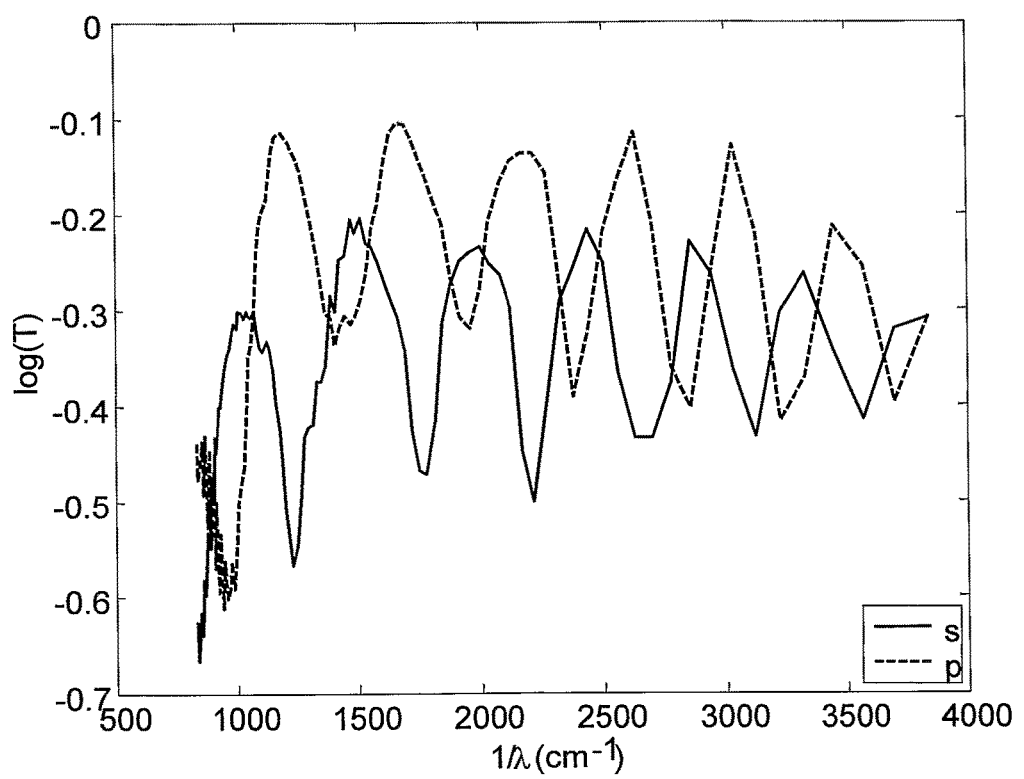
FIG. 9 shows the transmission (T) versus wave number (1/λ) as calculated by the FEM model (Model 2). The FEM structure is displayed in FIG. 5, and the bevel angle, $θ_B$ is 45° ($θ_1$=62.1°).
Figure 10A:
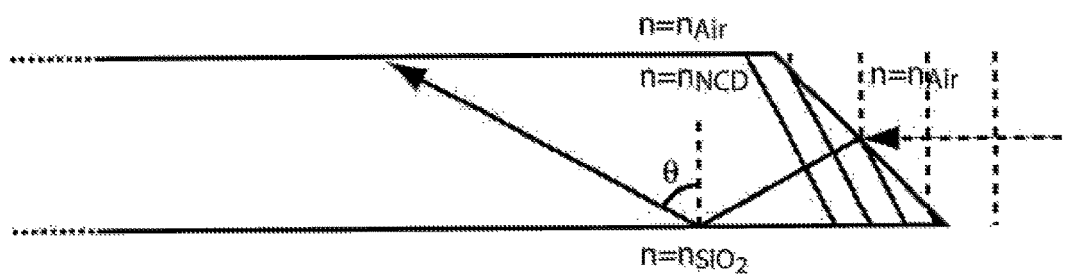
FIG. 10(a) shows a ray picture of the guided wave traveling with an angle of incidence θ in the waveguide slab.
Figure 10B:
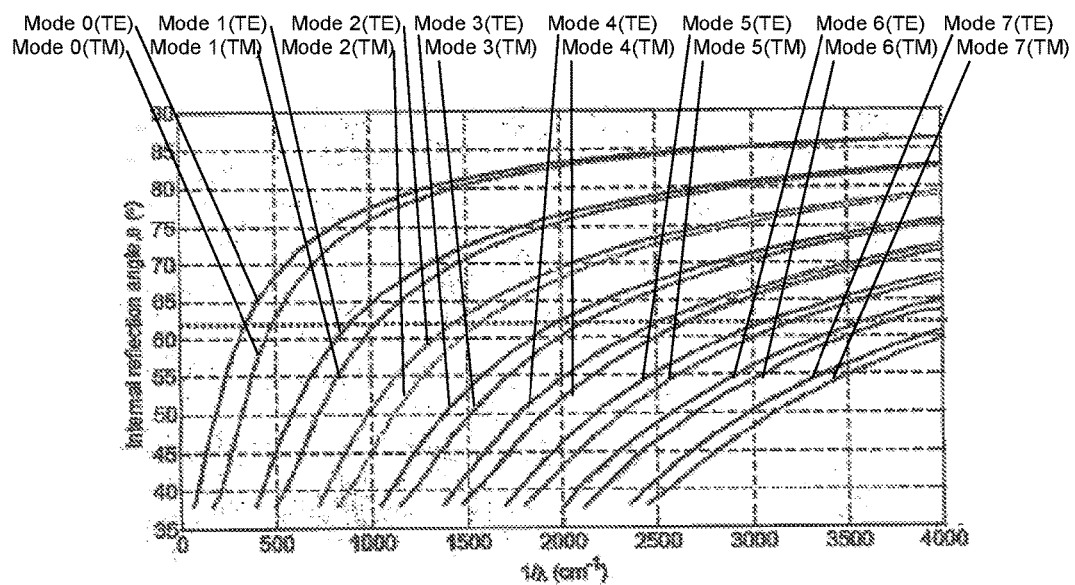
FIG. 10(b) shows a graph of wave vector angle of incidence (θ) versus wave number for the first few modes in the structure in FIG. 10(a). The modes were computed with model 1. The crossing of the dashed line with the dispersion curves for the various TE and TM modes indicates the predicted crests in the transmission spectrum with a bevel angle $θ_B$=45° (corresponding to a wave vector angle of incidence θ=62.1°).
Figure 11A:
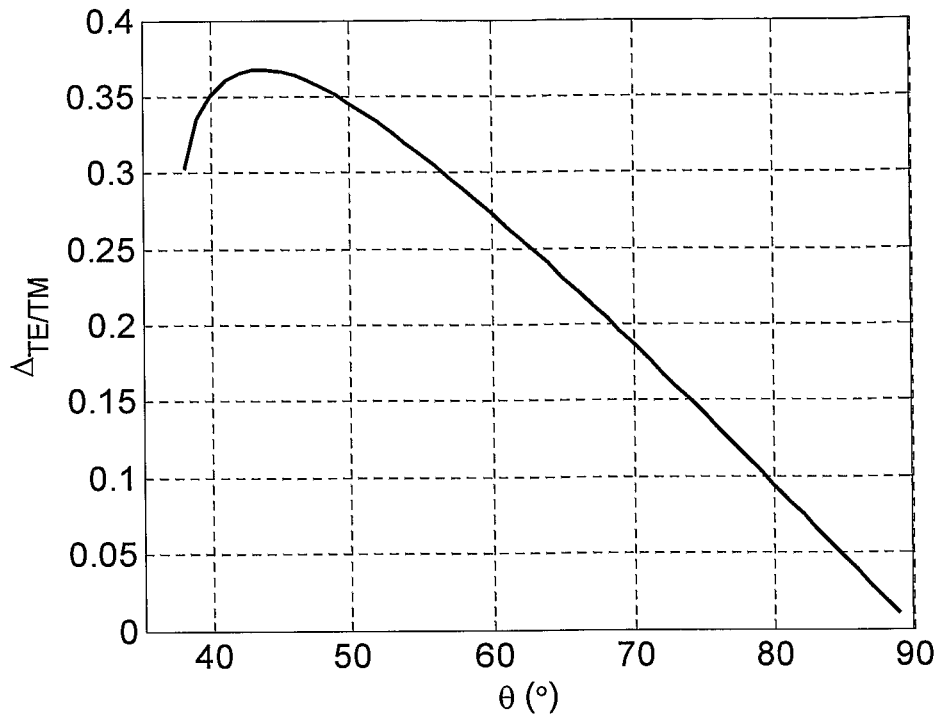
FIGS. 11a-11f show wave number shifts ΔTE/TM versus angle of incidence and bevel angle for a waveguide with $SiO_2$ and diamond thicknesses d=2 and 10 µm, respectively, as computed with Model 1 as described in the text with refractive index of the surrounding media n=1.0 (air.
Figure 11B:
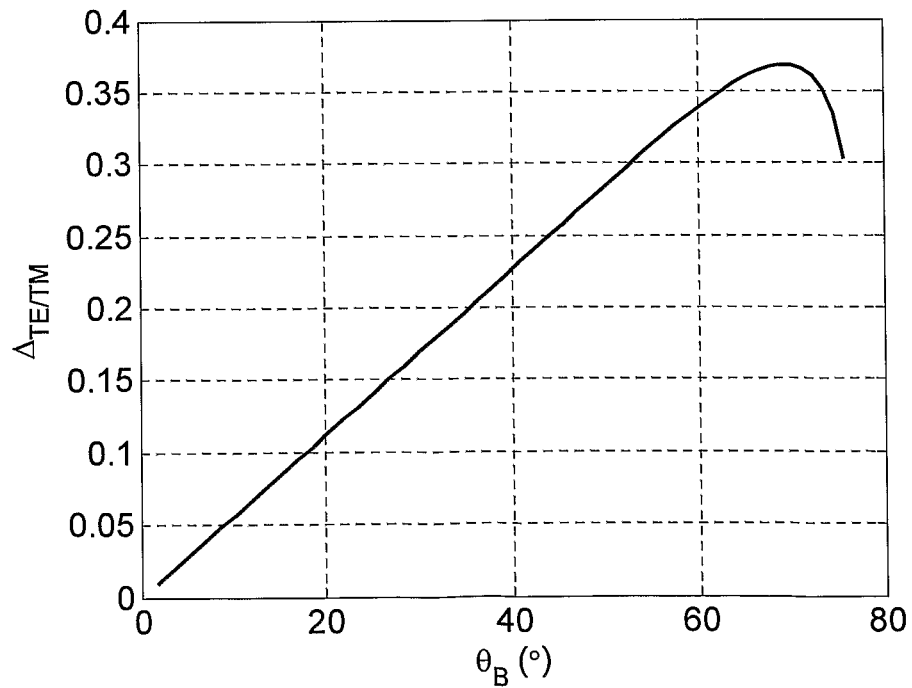
Figure 11C:
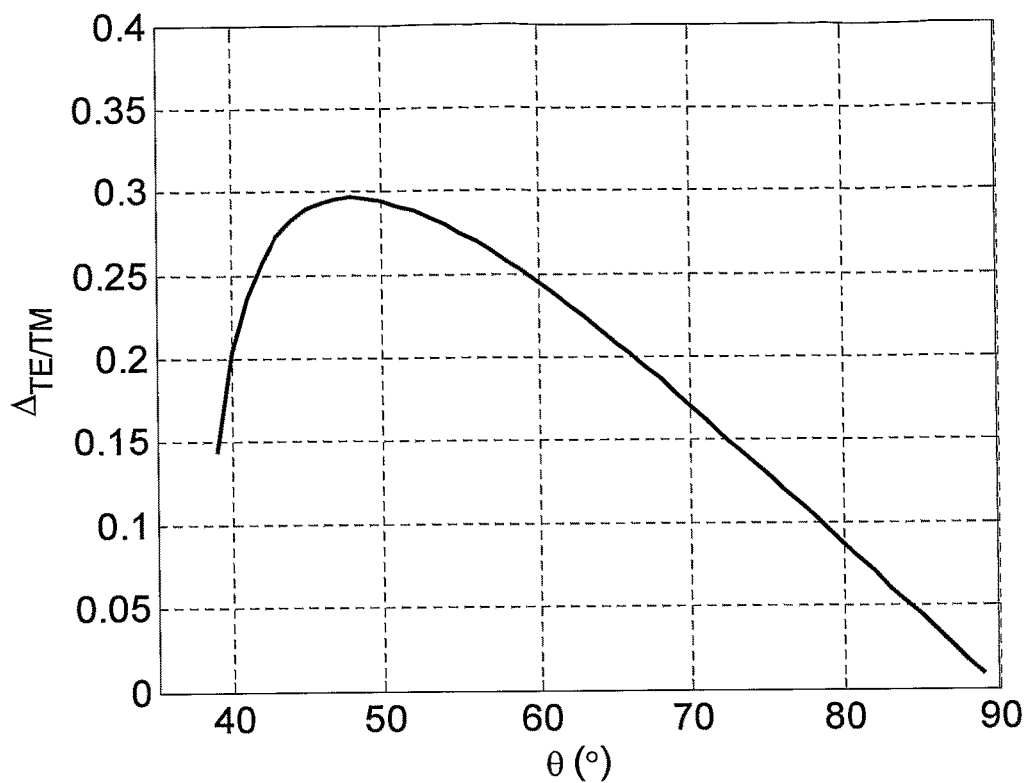
Figure 11D:
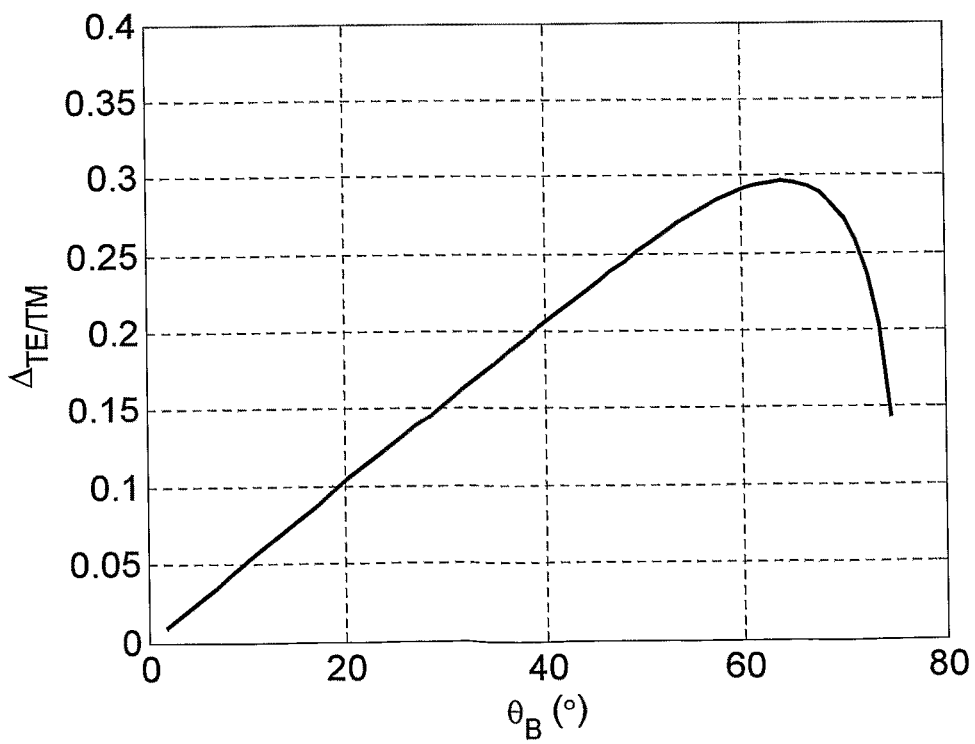
Figure 11E:
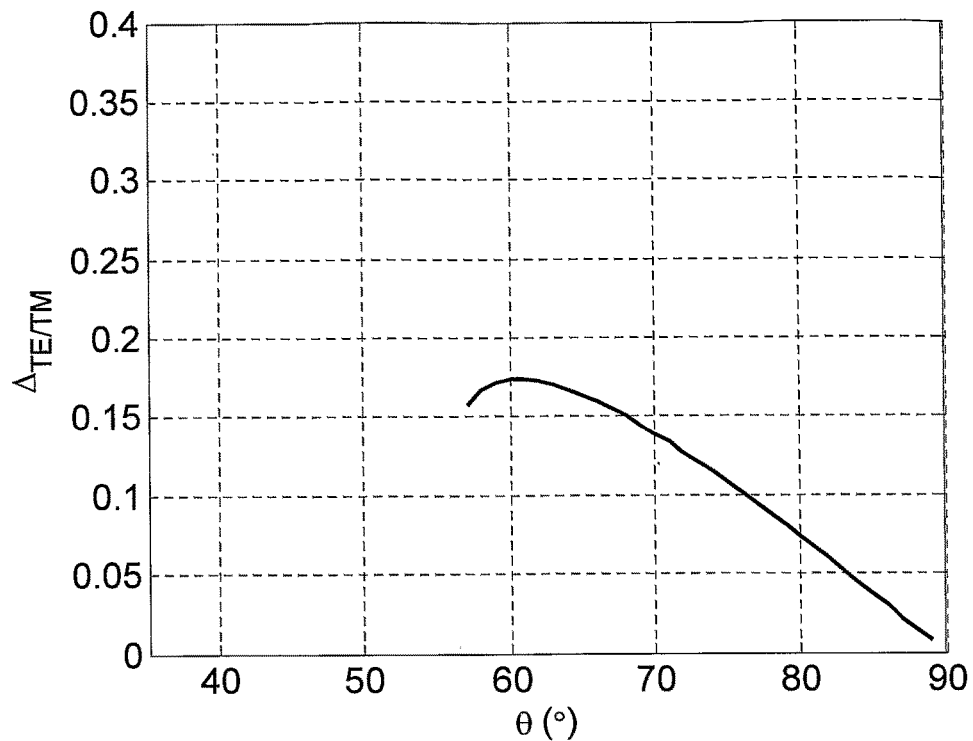
Figure 11F:
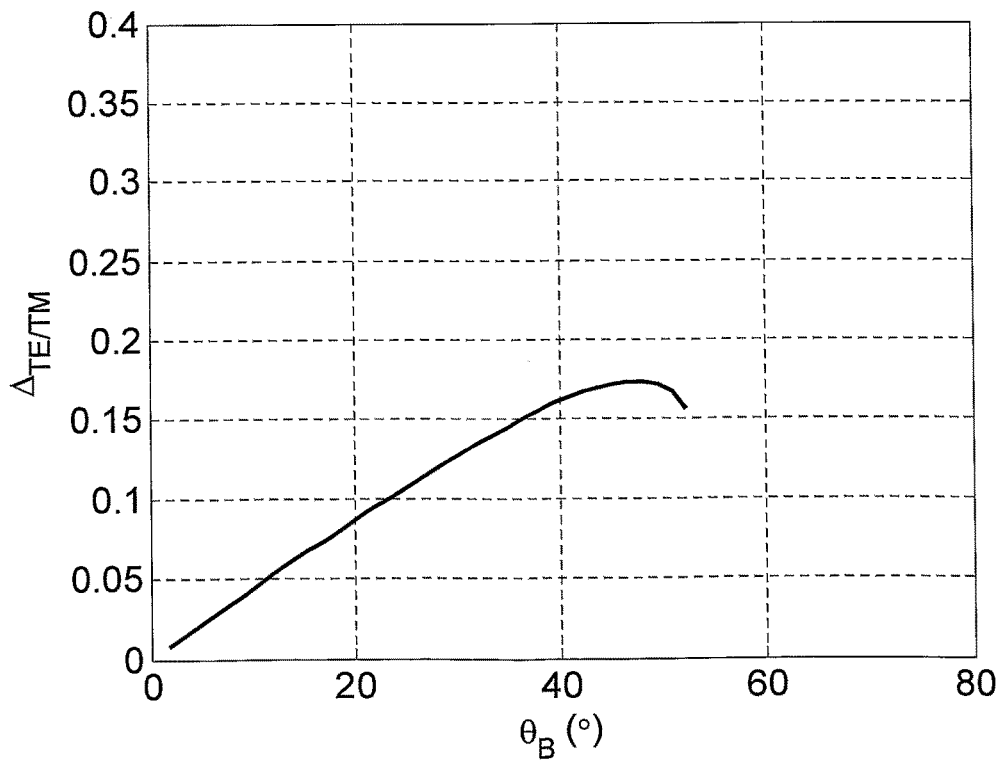
Figure 12:
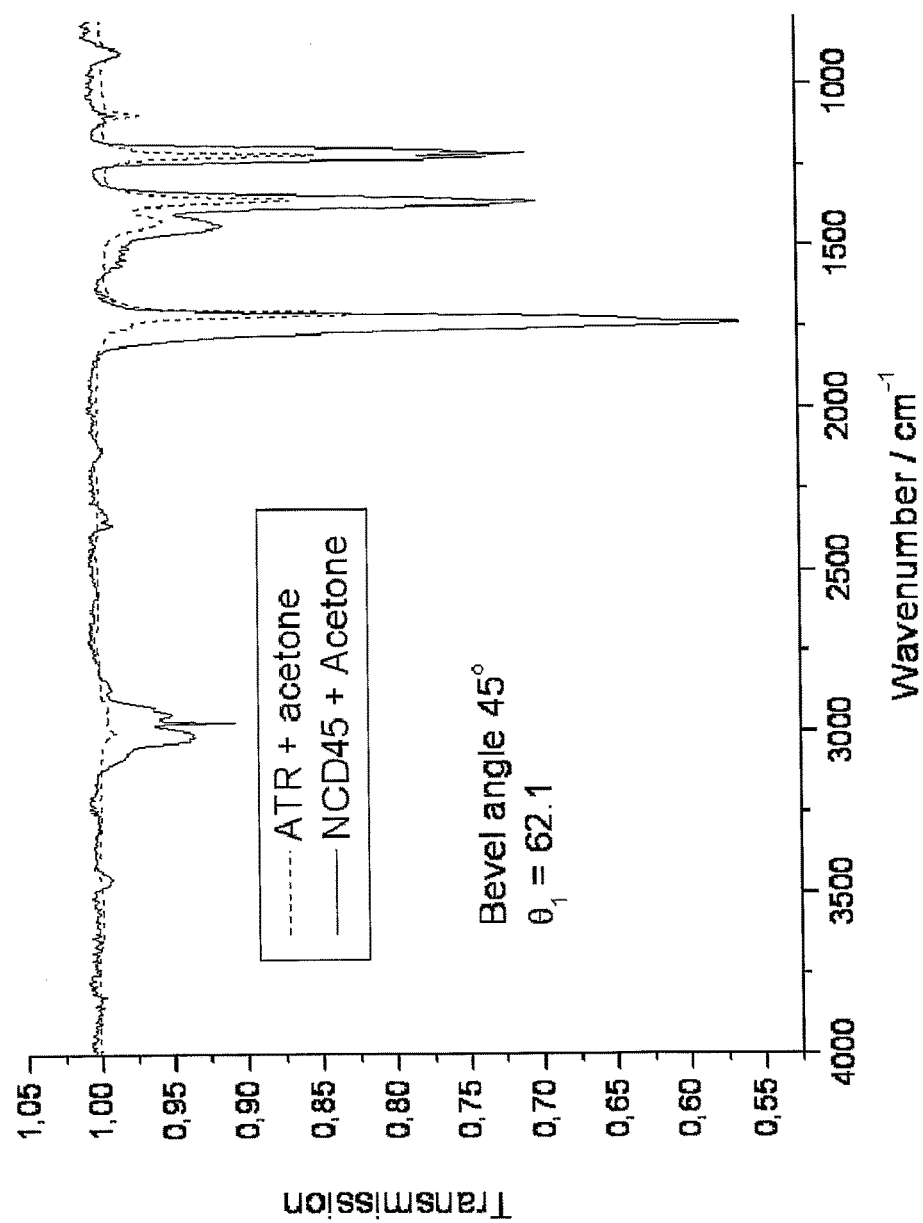
FIG. 12 shows EWS raw spectra of acetone obtained with NCD coated waveguide with bevel angle 45° and with a commercial single reflection diamond/ZnSe accessory (DuraSamplIR from SensIR Ltd) under similar experimental conditions using unpolarized mid-IR light.
Figure 13A:
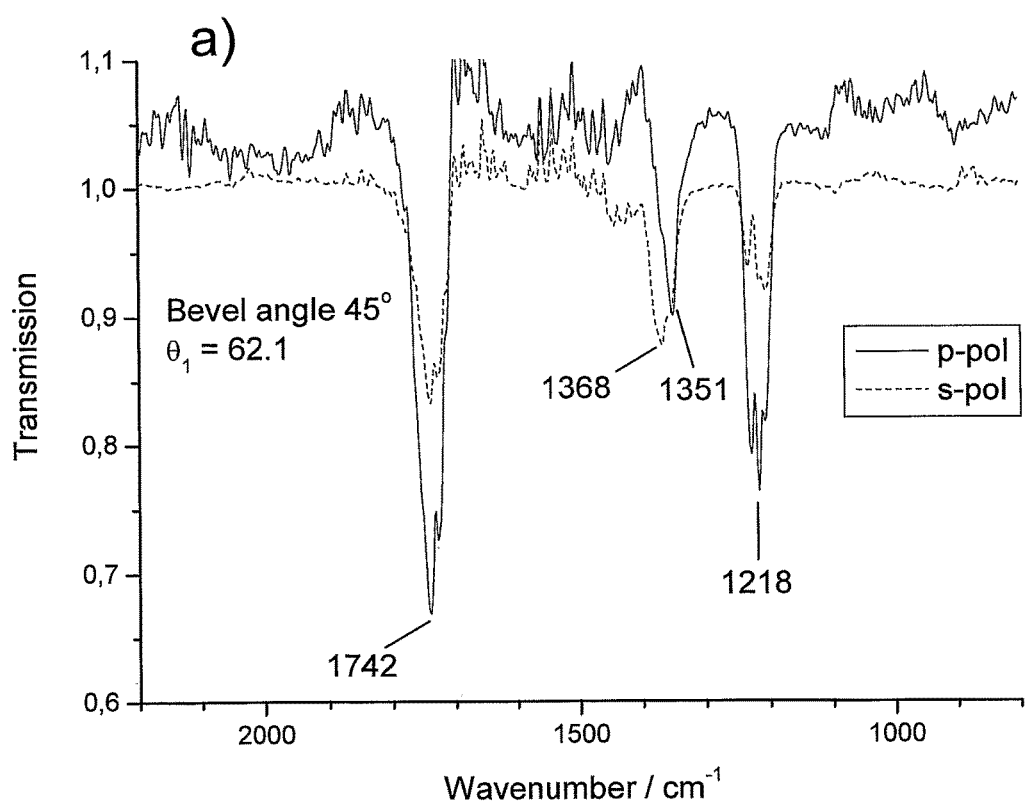
FIG. 13 (a and b) shows the EWS spectra of acetone on NCD coated waveguides with different bevel angles obtained in the polarization mode employing s- and p-polarized mid-IR light, respectively, which shows the potential of the methods to obtain additional structural information of adsorbed molecules.
Figure 13B:
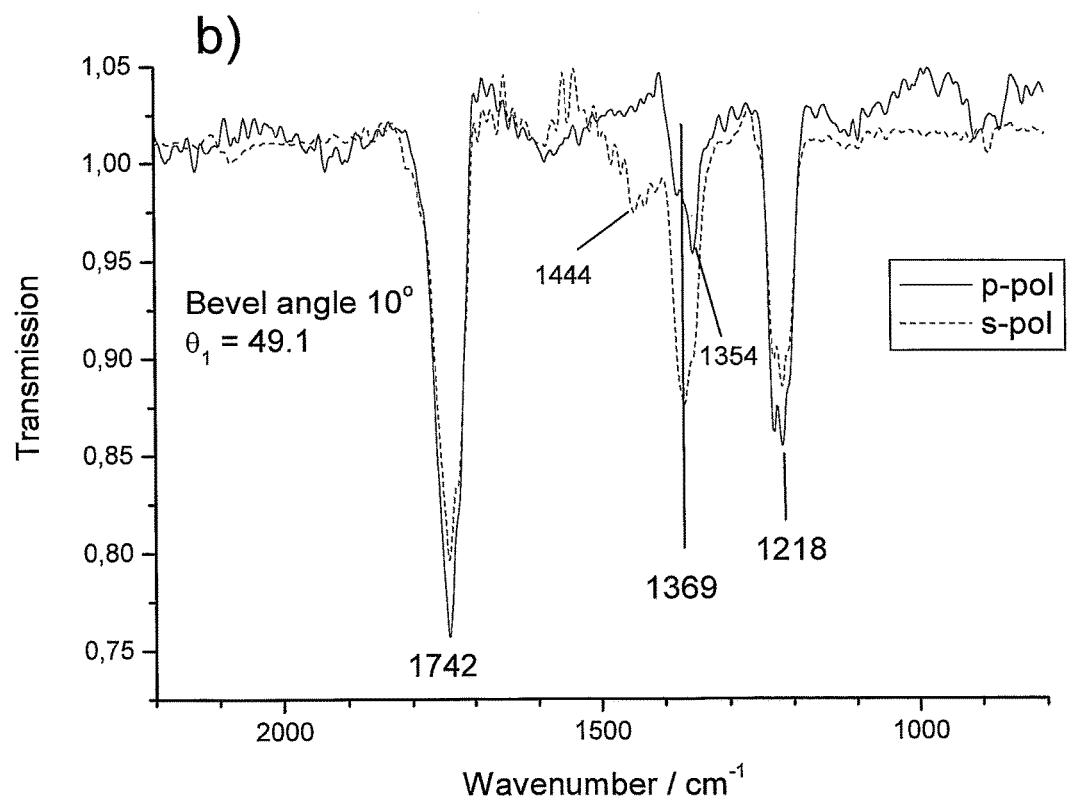

The transmission through the structure in FIG. 6, as computed with the FEM model is displayed in FIG. 9. Compared to the results from Model 1 we note the following. There is a strong "beat" pattern in the transmission. There is a crest in the transmission when the angle of the incident wave matches the angle of the wave vector of some mode in the slab. The idea is illustrated in FIG. 10. Using a ray model we use Snell's law to calculate the angle of incidence θ of the propagating wave in the waveguide. When a plane wave directed along the waveguide enters from air into the waveguide with $n_{NCD}$=2.4 we obtain $\theta_1$=62.1°. There will be a peak in the transmittance when this angle matches the angle of the wave vector of some mode in the waveguide. Thus, we show in FIG. 10 the angle of incidence θ of the wave vector of the first few modes in the waveguide, as calculated with Model 1. Note that there is a close agreement between the wave numbers where the modes cross θ=62.1° and the peak positions in FIG. 9. This suggests that it is possible to find an optimum θ (i.e., to find an optimum level of the horizontal "mode crossing" line) where the peaks of the s (TE) and p (TM) modes are completely out of phase creating a smoother unpolarized transmission spectrum. This idea was previously also discussed qualitatively by Plunkett and Braiman.[31] The average transmittance computed by the FEM model (log(T)=−0.3 in FIG. 10) is lower than that computed with Model 1 (log(T) =0) for large wave numbers in FIG. 7]. The reason is that the FEM model takes into account losses due to the non-ideal coupling between the incident plane wave and the modes in the wave guide, and also losses due to reflections at the exit port of the wave guide. This illustrates the importance of having smooth and possibly layered, refractive index-matched, entrance and exit surfaces of the planar waveguide. In FIG. 10, there is a slight decrease in the transmittance at small wave numbers. This is likely due to losses through the SiO$_2$ layer, which proves the importance of having a sufficiently thick cladding layer with much lower refractive index compared to the waveguide.

Example 4 describes the geometrical and materials dependence of mode mixing and polarization dependent transmission properties of the propagating light. It is expected that the "beat" pattern for unpolarized light is reduced if the "beat" patterns for s (TE) and p (TM) polarized light are out of phase. This is desirable from a practical viewpoint, and facilitates the spectral analysis. We define the shift of the s (TE) and p (TM) mode "beat" patterns as $$\Delta_{TE/TM} = \frac{(1/\lambda)_{TM,n} - (1/\lambda)_{TE,n}}{(1/\lambda)_{TE,n+1} - (1/\lambda)_{TE,n}} = \frac{(1/\lambda)_{TM,n} - (1/\lambda)_{TE,n}}{(1/\lambda)_{TM,n+1} - (1/\lambda)_{TM,n}} \quad (2)$$

An important question is how this shift is affected by different bevel angles $\theta_B$. We have used model 1 to investigate this dependence. Model 1 was applied to a waveguide structure with $t_{NCD}$=10.1 μm. The results are shown in FIGS. 11a-11f. Ideally we would like to have $\Delta_{TE/TM}$=0.5. However this is not possible for the present system. The maximum value $\Delta_{TE/TM}$≈0.37 is close to $\theta_B$69°.

There is a cut-off at some critical angle. Below (above) this critical value of θ ($\theta_B$) no modes can propagate. The critical angle corresponds to the situation where there is no longer total reflection at the NCD/SiO$_2$ interface. However, the critical angle might change when air is replaced by some other substance with an index of refraction which is larger than that for SiO$_2$. Since the results are approximate it might be wise to select a value of $\theta_B$ which is not too close to the critical angle. Otherwise there is a risk to end up with a device with poor transmission when air is replaced by some other investigated substance. This is of course highly desirable in practical applications. Of special interest is the case n=1.5 (water). To explicitly illustrate the effect of varying the substance on the NCD (layer 4 in FIG. 6), we show in FIGS. 11c-f the wave number shift $\Delta_{TE/TM}$ versus angle of incidence θ and versus bevel angle $\theta_B$ for a waveguides with layer 4 n=1.5 and n=2. In conclusion $\theta_B$ should be selected with care taking into account (a) that $\Delta_{TE/TM}$ should be as close to 0.5 as possible and (b) that if $\theta_B$ is too large there might be a risk that $\theta_B$ ends up above the critical bevel angle. In the present case, the waveguide should be tapered and have $\theta_B$ somewhere in the range 45°<$\theta_B$<60°. This should be a safe choice irrespective of analyte and surface functionalization.

REFERENCES

[1] C. E. Nebel, B. Rezek, D. Shin, H. Uetsuka, N. Yang, Journal of Physics D: Applied Physics 40 (2007) 6443-6466.
[2] B. R. Eggins, Chemical sensors and biosensors, Chichester, John Wiley & Sons, 2002.
[3] F. Rathgeb, G. Gauglitz, in: R. A. Meyers (Ed.), Encyclopedia of Analytical Chemistry, 2000.
[4] R. B. Thompson, Fluorescence Sensors and Biosensors, Boca Raton, CRC Press, 2006.
[5] N. J. Harrick, Internal Reflection Spectroscopy, John Wiley & Sons, 1967.
[6] F. M. Mirabella, Modern Techniques in Applied Molecular Spectroscopy, New York, John Wiley & Sons, 1998.
[7] R. Siebert, J. Muller, Sensors and Actuators A: Physical 119 (2005) 584-592.
[8] R. Siebert, J. Muller, Sensors and Actuators A: Physical 119 (2005) 138-149.
[9] N. Branan, T. A. Wells, Vibrational Spectroscopy 44 (2007) 192-196.
[10] T. Buffeteau, E. Le Calvez, B. Desbat, I. Pelletier, M. Pezolet, Journal of Physical Chemistry B 105 (2001) 1464-1471.
[11] W. Liao, F. Wei, D. Liu, M. X. Qian, G. Yuan, X. S. Zhao, Sensors and Actuators B: Chemical 114 (2006) 445-450.
[12] P. Rigler, W.-P. Ulrich, P. Hoffmann, M. Mayer, H. Vogel, Chem Phys Chem 4 (2003) 268-275.
[13] M. S. Schneider, J. D. Grunwaldt, T. Burgi, A. Baiker, Review of Scientific Instruments 74 (2003) 4121-4128.
[14] V. I. Konov, E. D. Obraztsova, S. M. Pimenov, V. G. Ralchenko, A. A. Smolin, A. V. Khomich, V. I. Polyakov, A. I. Rukovishnikov, P. I. Perov, E. N. Loubnin, SPIE 2428 (1995) 612-620.

[15] V. N. Khabashesku, J. L. Margrave, E. V. Barrera, Functionalized carbon nanotubes and nanodiamonds for engineering and biomedical applications, Elsevier Science Sa, 2005, 859-866.

[16] A. Härtl, E. Schmich, J. A. Garrido, J. Hernando, S. C. R. Cathrino, S. Walter, P. Feulner, A. Kromka, D. Steinmuller, M. Stutzmann, Nature Materials 3 (2004) 736-742.

[17] W. S. Yang, et al., Nature Materials 1 (2002) 253-257.

[18] Z. Remes, A. Choukourov, J. Stuchlik, J. Potmesil, M. Vanecek, Diamond and Related Materials 15 (2006) 745-748.

[19] O. A. Williams, M. Daenen, J. D'Haen, K. Haenen, J. Maes, V. V. Moshchalkov, M. Nesladek, D. M. Gruen, Diamond and Related Materials Diamond 2005 15 (2006) 654-658.

[20] G. Reiter, N. Hassler, V. Weber, D. Falkenhagen, U. P. Fringeli, Biochimica Et Biophysica Acta-Proteins and Proteomics 1699 (2004) 253-261.

[21] P. Wenzl, M. Fringeli, J. Goette, U. P. Fringeli, Langmuir 10 (1994) 4253-4264.

[22] K. K. Chittur, Biomaterials 19 (1998) 357-369.

[23] M. L. Clarke, J. Wang, Z. Chen, Journal of Physical Chemistry B 109 (2005) 22027-22035.

[24] Y. Yokoyama, R. Ishiguro, H. Maeda, M. Mukaiyama, K. Kameyama, K. Hiramatsu, Journal of Colloidal Science 268 (2003) 23-32.

[25] P. Rigler, W.-P. Ulrich, R. Hovius, E. Ilegems, H. Pick, H. Vogel, Biochemistry 42 (2003) 14017-14022.

[26] C. Vigano, E. Goormaghtigh, J. M. Ruysschaert, Detection of structural and functional asymmetries in P-glycoprotein by combining mutagenesis and H/D exchange measurements, Elsevier Sci Ireland Ltd, 2003, 121-135.

[27] B. M. Smith, S. E. Lappi, S. H. Brewer, S. Dembowy, J. Belyea, S. Franzen, Langmuir 20 (2004) 1184-1188.

[28] A. Nabok, S. Haron, A. Ray, Registration of heavy metal ions and pesticides with ATR planar waveguide enzyme sensors, Elsevier Science Bv, 2004, 423-428.

[29] P. O. Andersson, M. Lundquist, L. Tegler, S. Börjegren, L. Baltzer, L. Österlund, CHEMPHYSCHEM 8 (2007) 712-722.

[30] E. M. Kosower, G. Markovich, Y. Raichlin, G. Borz, A. Katzir, Journal of Physical Chemistry B 108 (2004) 12633-12636.

[31] S. E. Plunkett, M. S. Braiman, Applied Optics 36 (1997) 4055-4061.

[32] J. Vongsvivut, S. V. Shilov, S. Ekgasit, M. S. Braiman, Applied Spectroscopy 56 (2002) 1552-1561.

[33] W. S. C. Chang, K. Loh, Applied Optics 10 (1971) 2361.

[34] M. Karlsson, K. Hjort, F. Nikolajeff, Optics Letters 26 (2001) 1752-1754.

[35] COMSOL Multiphysics, version 3.3, http://www.comsol.se.

The invention claimed is:

1. Optical sensor unit for infra red evanescence wave spectroscopy, IR-EWS, analysis of chemical and biological substances in an analyte, comprising a waveguide with a sensor surface to be put into contact with the analyte, wherein the sensor surface is provided with an affinity enhancing layer of nano-crystalline diamond, NCD, which is physically or chemically bound to the waveguide, and wherein the waveguide is comprised of diamond having a refractive index above 2 with respect to light in the infrared range.

2. Optical sensor unit according to claim 1, wherein the waveguide is thin enough to achieve mode selected propagating waves when light of infrared wavelengths is transmitted through the optical sensor unit.

3. Optical sensor unit according to claim 1, comprising an in-coupling element and an out-coupling element, wherein at least one of said elements is integrated with the waveguide.

4. Optical sensor unit according to claim 1, comprising a substrate member with at least one waveguide formed at a first surface thereof, and wherein the sensor surface of the waveguide provided with the affinity enhancing layer is exposed in an associated recess formed in the opposite substrate surface.

5. Optical sensor unit according to claim 4, wherein the substrate is a silicon wafer, and the waveguide is comprised of diamond that is deposited on an intermediate cladding layer on the first substrate surface.

6. Infra red evanescence wave spectroscopy system comprising an optical sensor unit according to claim 1.

7. Internal reflection element, IRE, for attenuated total reflection, ATR, infrared spectroscopy analysis of chemical and biological substances in an analyte, comprising a waveguide with a sensor surface to be put into contact with the analyte, wherein the sensor surface of the waveguide is comprised of nano-crystalline diamond, NCD, which is physically or chemically bound to a remainder of the waveguide, and wherein the remainder of the waveguide is comprised of diamond having a refractive index above 2 with respect to light in the infrared range.

8. Optical sensor unit according to claim 1, wherein the waveguide is comprised of poly-crystalline diamond.

9. Optical sensor unit according to claim 1, wherein a thickness of the waveguide is within 5-30 µm.

10. Optical sensor unit for infra red evanescence wave spectroscopy, IR-EWS, analysis of chemical and biological substances in an analyte, comprising a waveguide with a sensor surface to be put into contact with the analyte, wherein the sensor surface is provided with an affinity enhancing layer of nano-crystalline diamond, NCD, physically or chemically bound to the waveguide, and wherein the waveguide is comprised of diamond having a refractive index higher than surrounding media with respect to light in the infrared range.

11. Optical sensor unit according to claim 1, wherein the affinity enhancing layer is comprised of ultra-nano-crystalline diamond, UNCD.

12. Optical sensor unit for infra red evanescence wave spectroscopy, IR-EWS, analysis of chemical and biological substances in an analyte, comprising a waveguide formed of poly-crystalline diamond and having an optical sensor surface through which energy from light propagating within the waveguide is absorbed, and an affinity enhancing layer of nanocrystalline diamond, NCD, formed on the waveguide sensor surface.

13. Optical sensor unit according to claim 12, wherein the NCD layer has a thickness of 0.1 µm.

14. Method of producing an optical sensor unit comprising the steps:
  i) depositing an optical cladding layer on a first surface of a substrate,
  ii) depositing at least one diamond waveguide on the optical cladding layer,
  iii) forming a recess associated with each diamond waveguide in the second, opposite, surface of the substrate through the cladding layer, to expose a section of the diamond waveguide surface from the side of said second surface, and iv) depositing an affinity enhancing layer on the exposed section of the diamond waveguide forming a sensor surface.

15. Method according to claim 14, wherein the substrate is comprised of silicon.

16. Method according to claim 14, wherein the affinity enhancing layer is comprised of nano-crystalline diamond, NCD.

17. Method according to claim 15, wherein the affinity enhancing layer is comprised of nano-crystalline diamond, NCD.

* * * * *